United States Patent [19]
Findlay et al.

[11] Patent Number: 5,204,323
[45] Date of Patent: Apr. 20, 1993

[54] HEPARIN AND HIRUDIN ANTIDOTAL COMPOSITIONS AND METHODS

[75] Inventors: Valerie S. Findlay; Roger Kerry, both of Horsham; Graham F. Pay, Patcham; Robert B. Wallis, Leechponds Hills; Keith D. Butler, Soreham-by-Sea, all of England

[73] Assignee: Ciba-Geigy Corporation, Ardsley, N.Y.

[21] Appl. No.: 763,477

[22] Filed: Sep. 20, 1991

Related U.S. Application Data

[63] Continuation of Ser. No. 416,882, Oct. 4, 1989, abandoned.

[30] Foreign Application Priority Data

Oct. 6, 1988 [GB] United Kingdom ................ 8823480

[51] Int. Cl.$^5$ .................... A61K 37/02; A61K 31/725
[52] U.S. Cl. ........................................ 514/2; 514/12; 514/56; 514/54; 514/834; 530/383
[58] Field of Search ................ 514/2, 12, 56, 802, 514/834; 530/383

[56] References Cited

U.S. PATENT DOCUMENTS 4,789,733 12/1988 Winkelman .............................. 514/8
4,929,602 5/1990 Harker et al. ......................... 514/18

FOREIGN PATENT DOCUMENTS 0229234 7/1987 European Pat. Off. .

OTHER PUBLICATIONS

Agnelli et al.; Chemical Abstracts 111(15):1273825 (1989).
Palmer et al.; Chemical Abstracts 109(25):222834h (1988).
Koehler et al.; Chemical Abstracts 109(7):512220 (1988).
Rock et al.; Chemical Abstracts 95(19):162771r (1981).
Rock et al.; Vox Sang. 41:56–60 (1981).
Palmer et al.; Transfusion 28(4):311–315 (1988).
Agnelli et al; Thrombosis and Haemostasis 61(3):507–510 (1989).
Thrombos. Diather Haemorrh. vol. 14, No. 32 p. 32 (1965).
Textbook of Medical Physiology, Arthur C. Guytan, MD pp. 140–141.
Clinical Science 67, 561–567 (1984) Peake.
Nature 312, 337–342 (1984) Vehar et al.
Critical Reviews Ancol./Hermatol. 6, 19–54 (1985) Hamer et al.
Clinical Pharma cokinetics 13, 365–380 Messori et al. (1987).
Blut 56, 171–178(1988) Fukui et al.
Hemeostasis and Thrombosis 8, 19–45 (1986) Mannucci.
Amer. J. Hematol 30, 154–157 (1989) Wigermans et al.
Amer. J. Hematol 31, 32–35 (1989) Vigano et al.
Pharma zeutische Chemie (1982) Schröder et al. pp. 650–659.
The Lancet 1,1145–1148 (1984) Kobrinsky et al.
Die Pharmayie 36, 653–660 (1981).

Primary Examiner—Johnnie R. Brown
Assistant Examiner—Nancy S. Carson
Attorney, Agent, or Firm—Irving M. Fishman; Karen G. Kaiser

[57] ABSTRACT

The invention provides an antidote to blood anticoagulants comprising Factor VIII or fragments of Factor VIII which retain its activity or a substance which increases its concentration in blood.

10 Claims, 12 Drawing Sheets

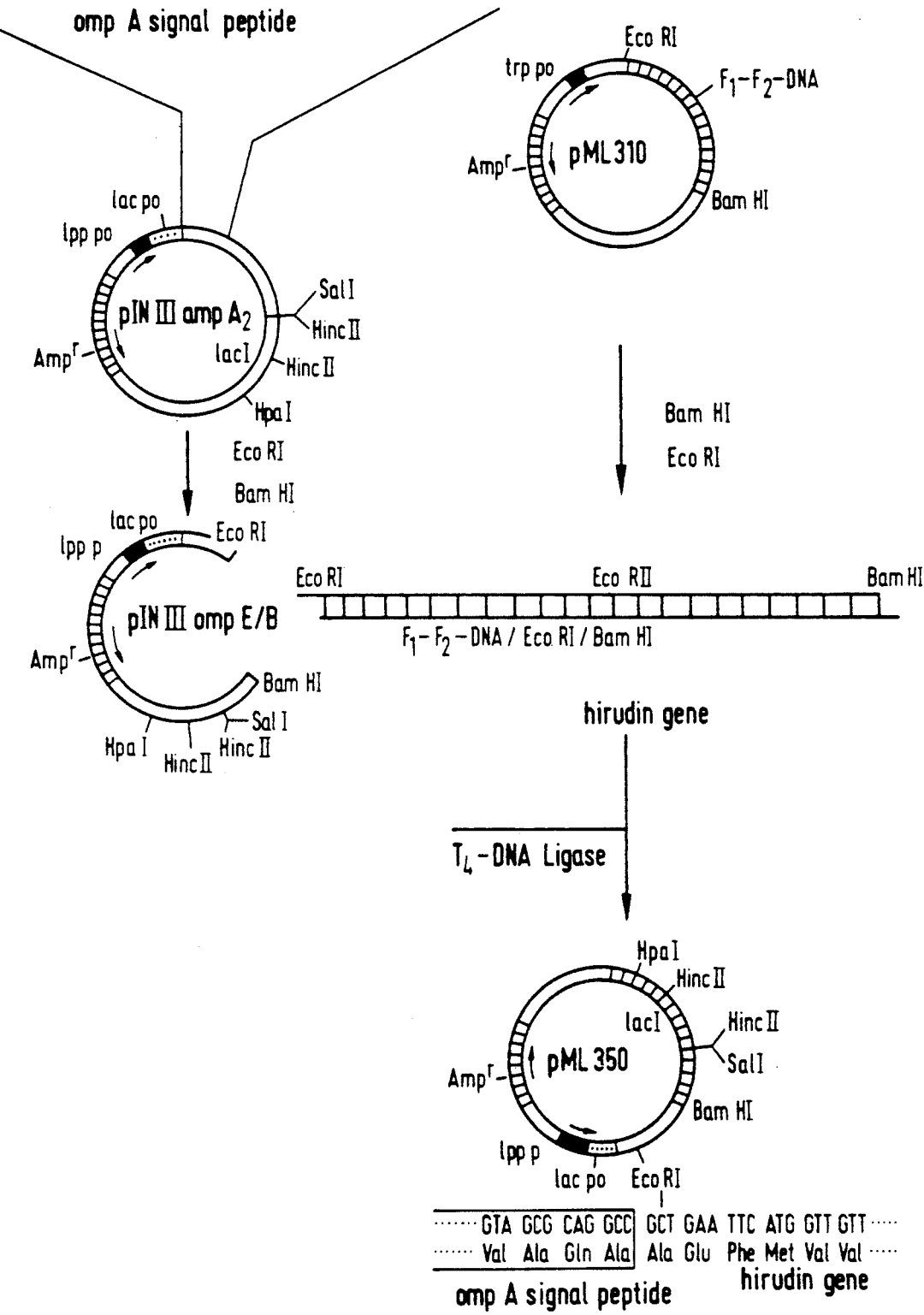

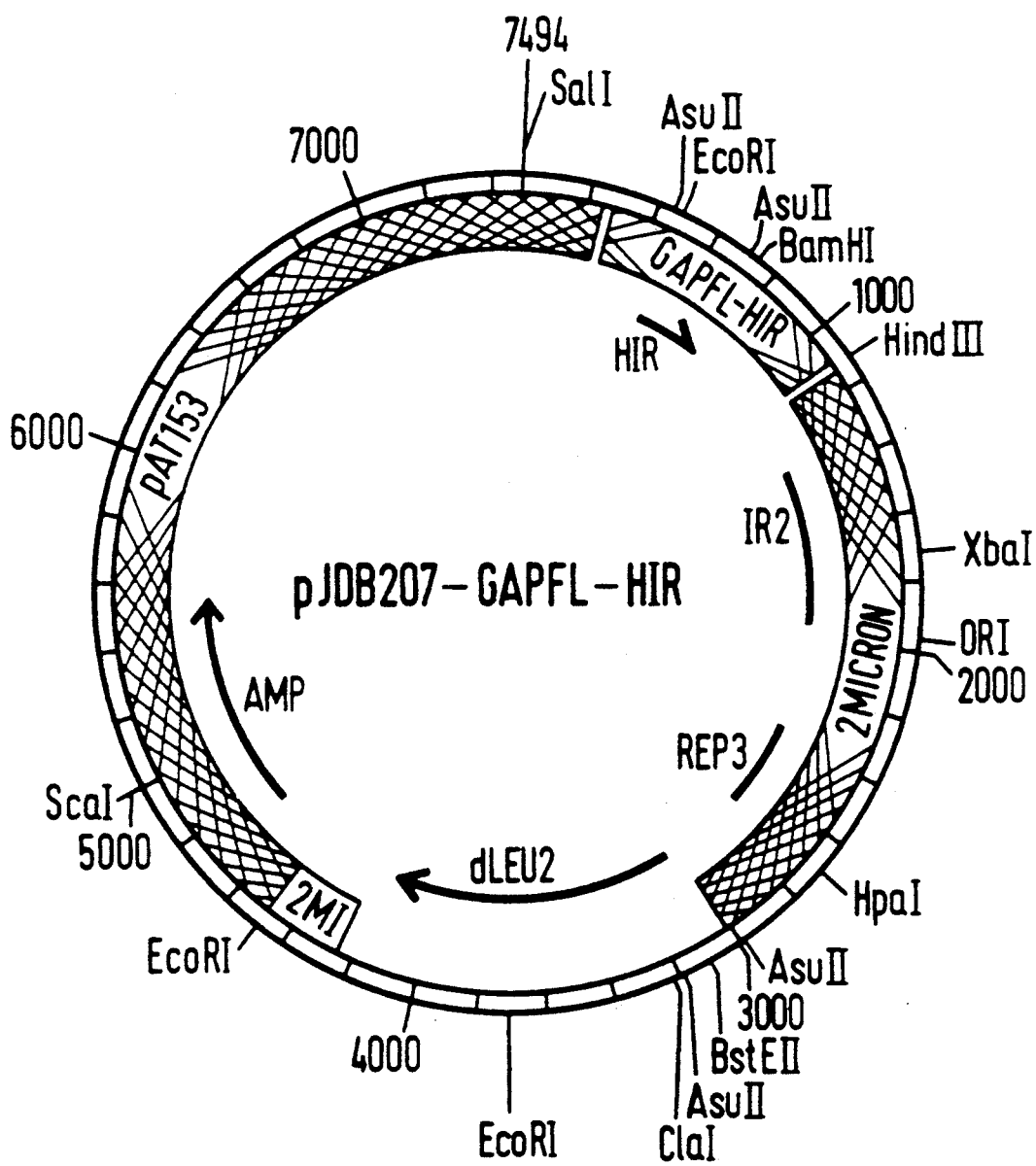
Fig. 2: Plasmid map of plasmid pJDB207/GAPFL-HIR

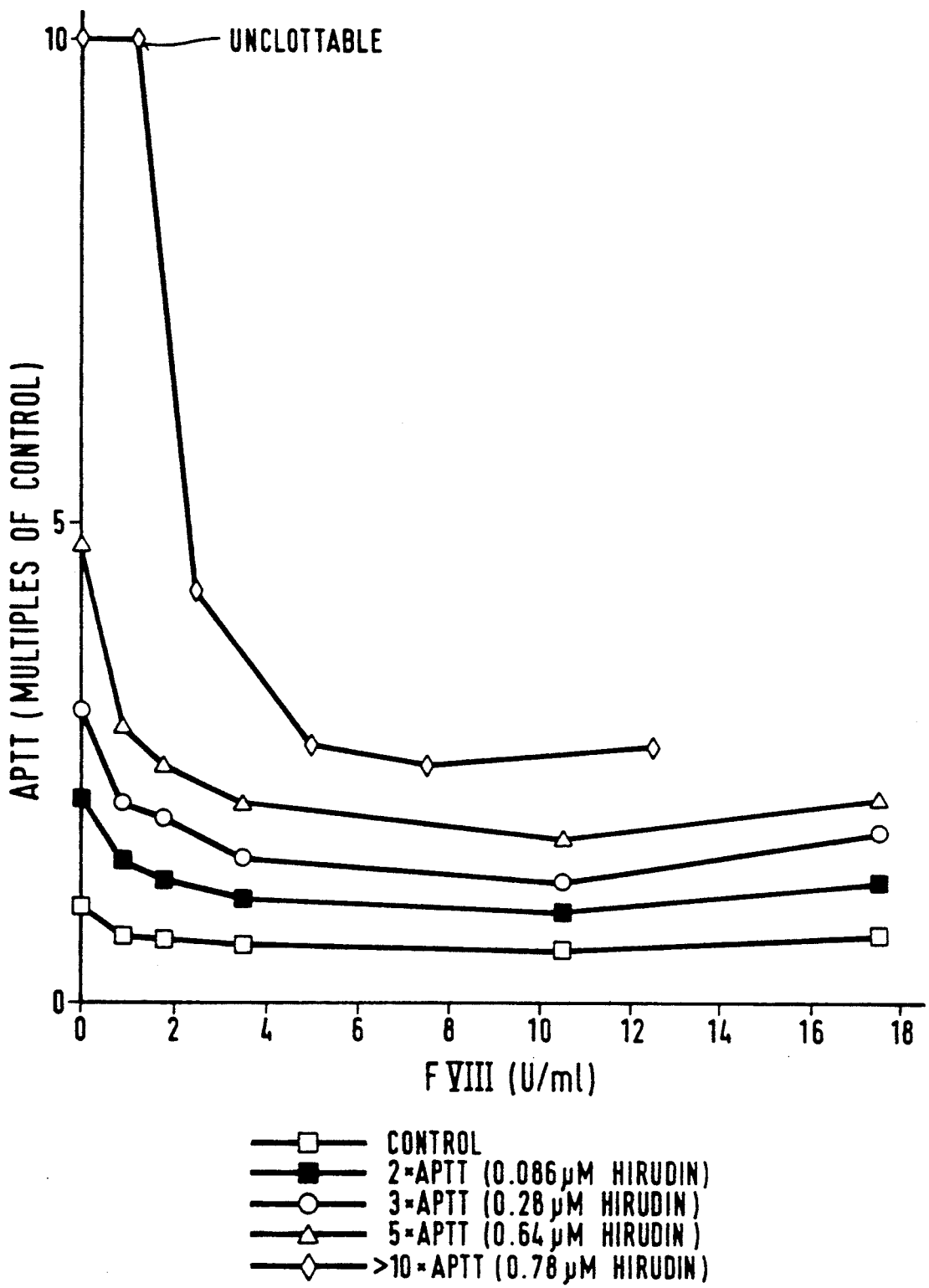

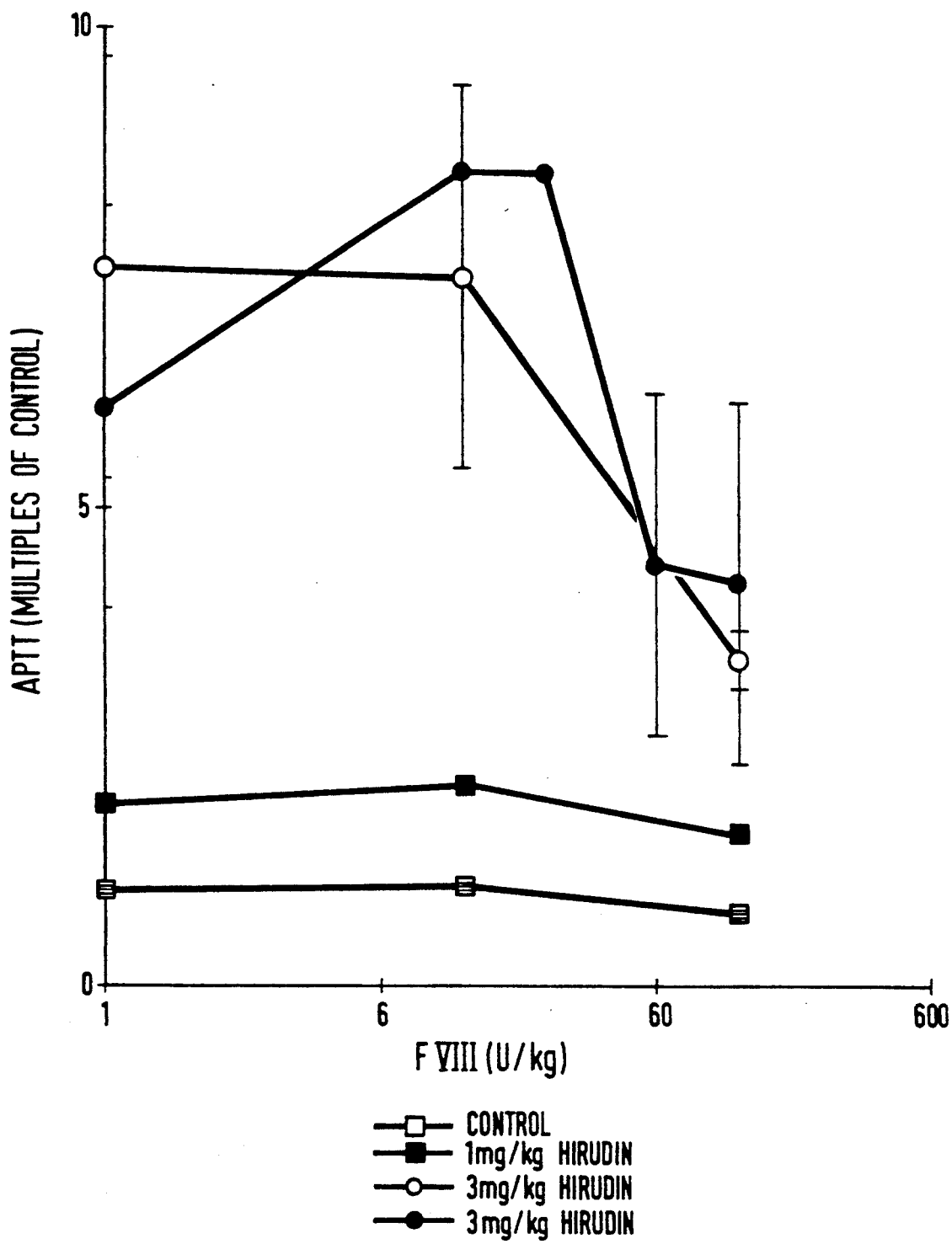

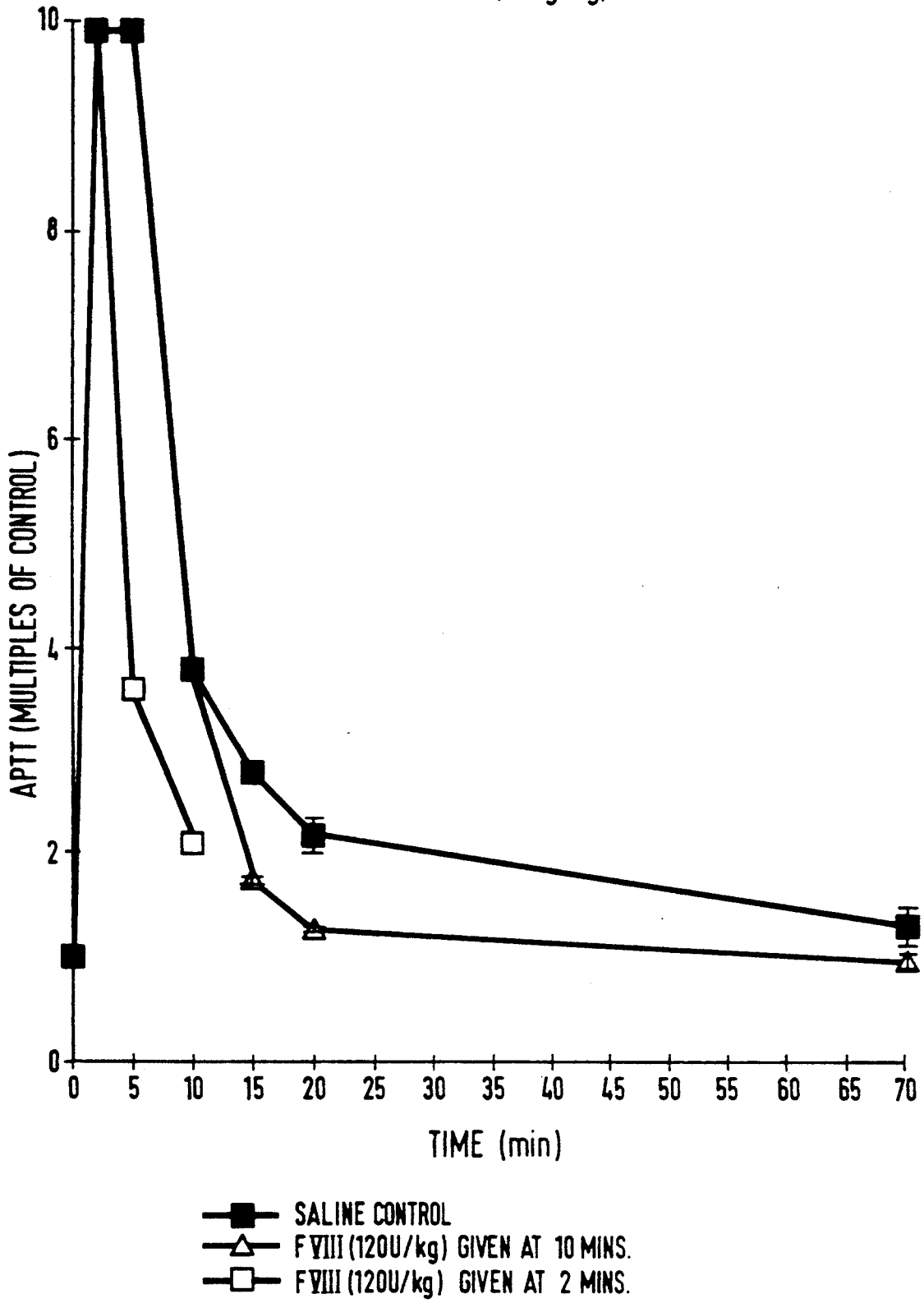

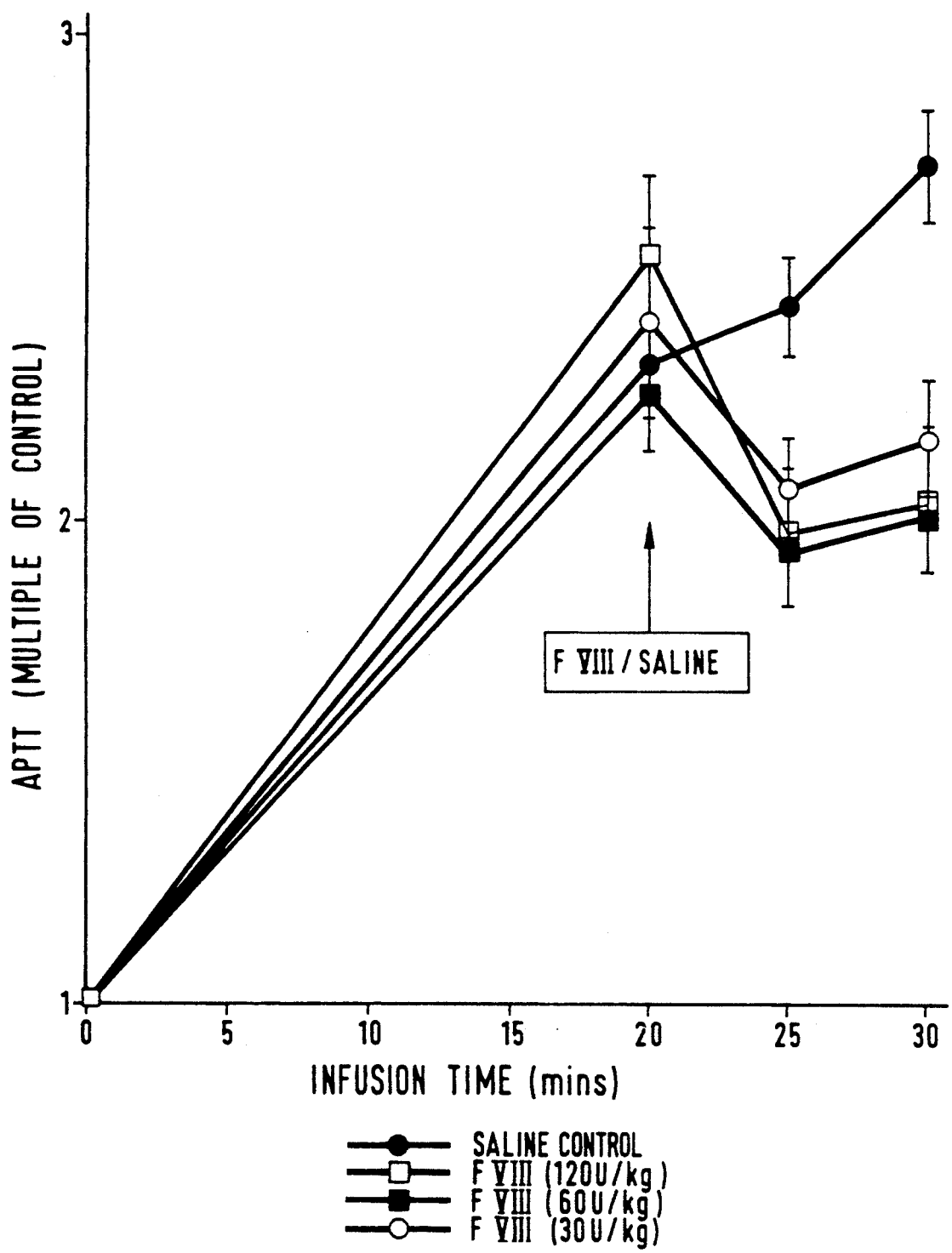

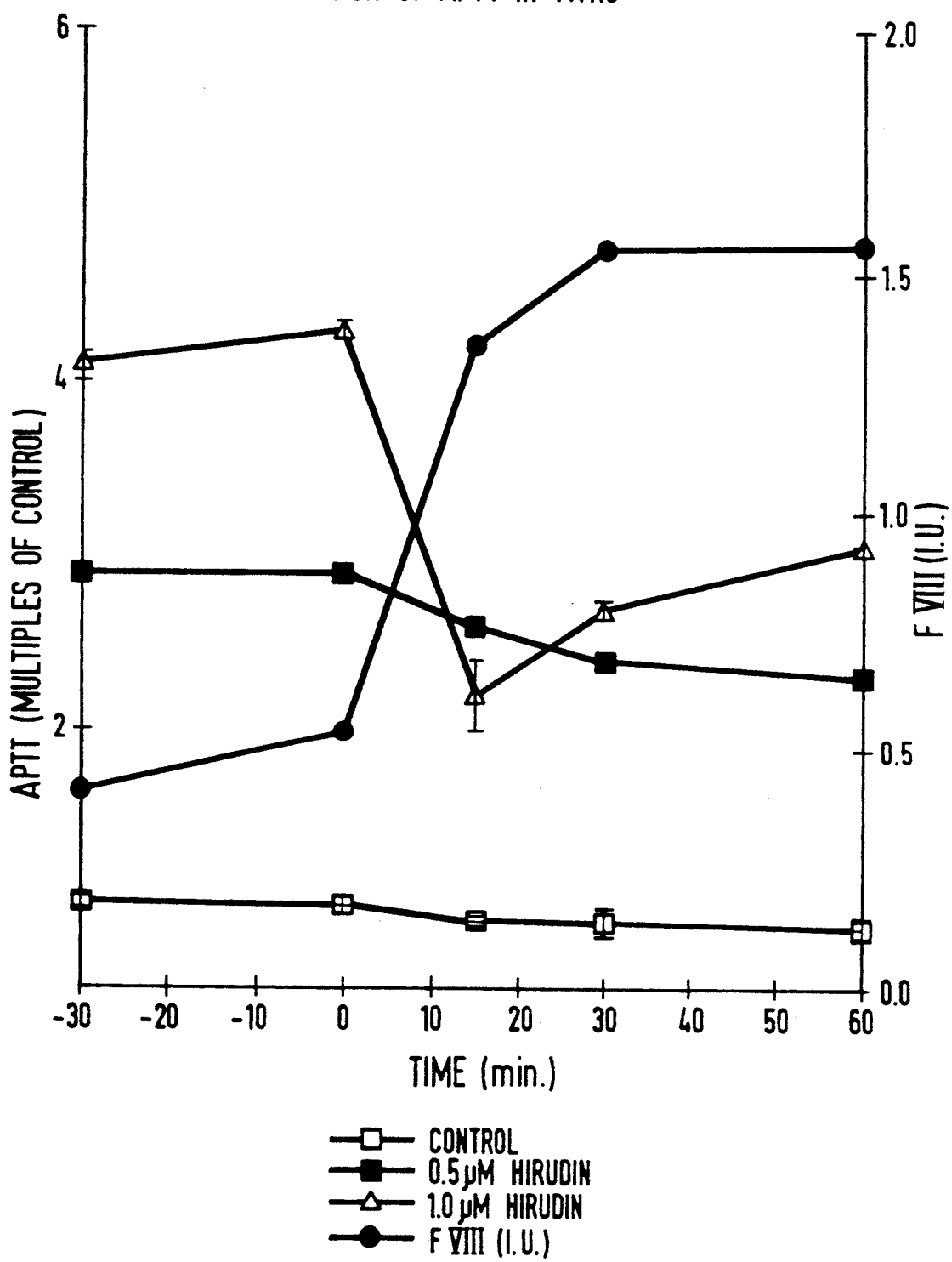
Fig. 7 IN VITRO EFFECT OF DDAVP INFUSION ON F VIII LEVELS IN HUMAN PLASMA AND THE CORRESPONDING EFFECT ON HIRUDIN INDUCED ELEVATION OF APTT IN VITRO

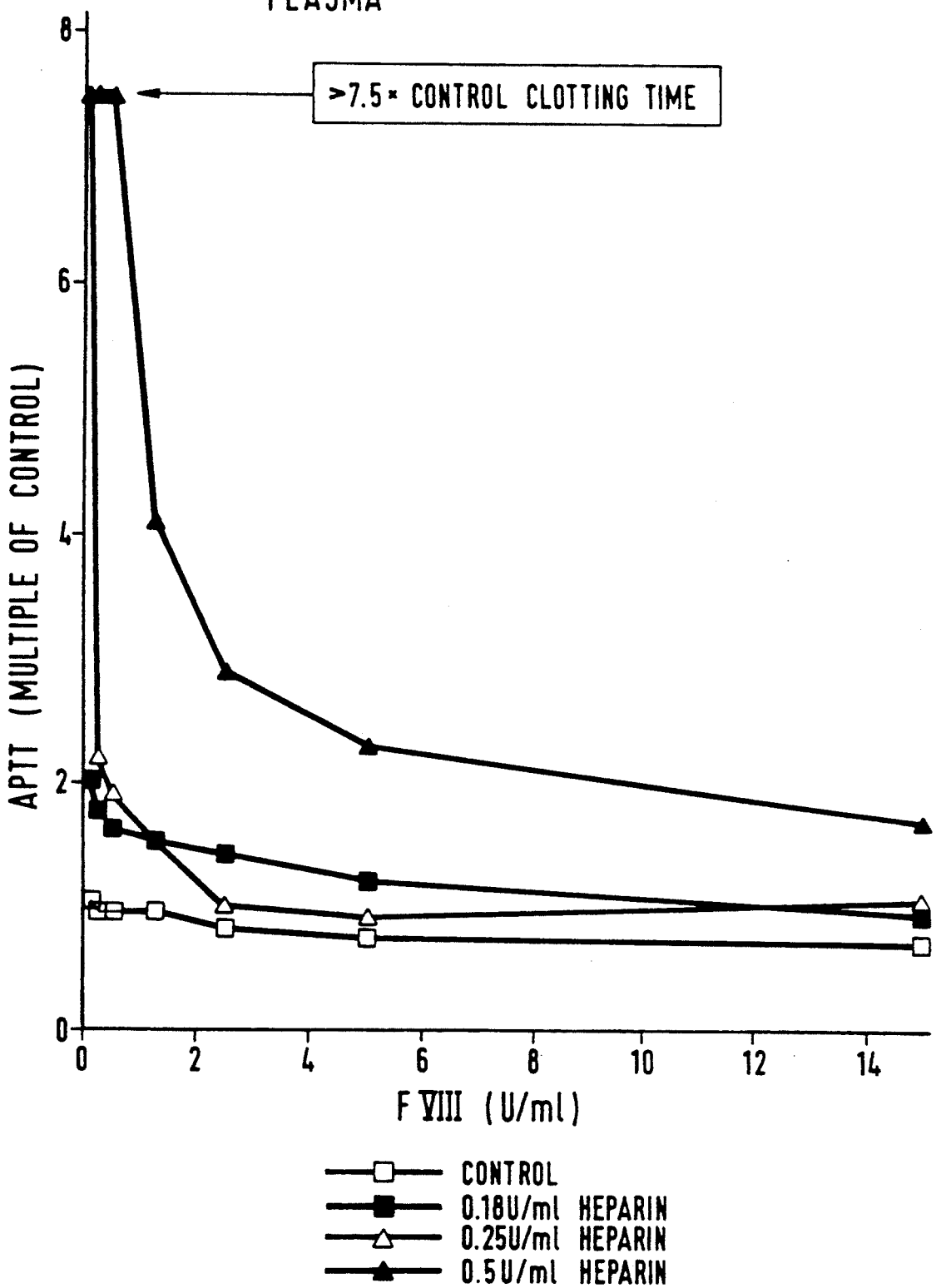

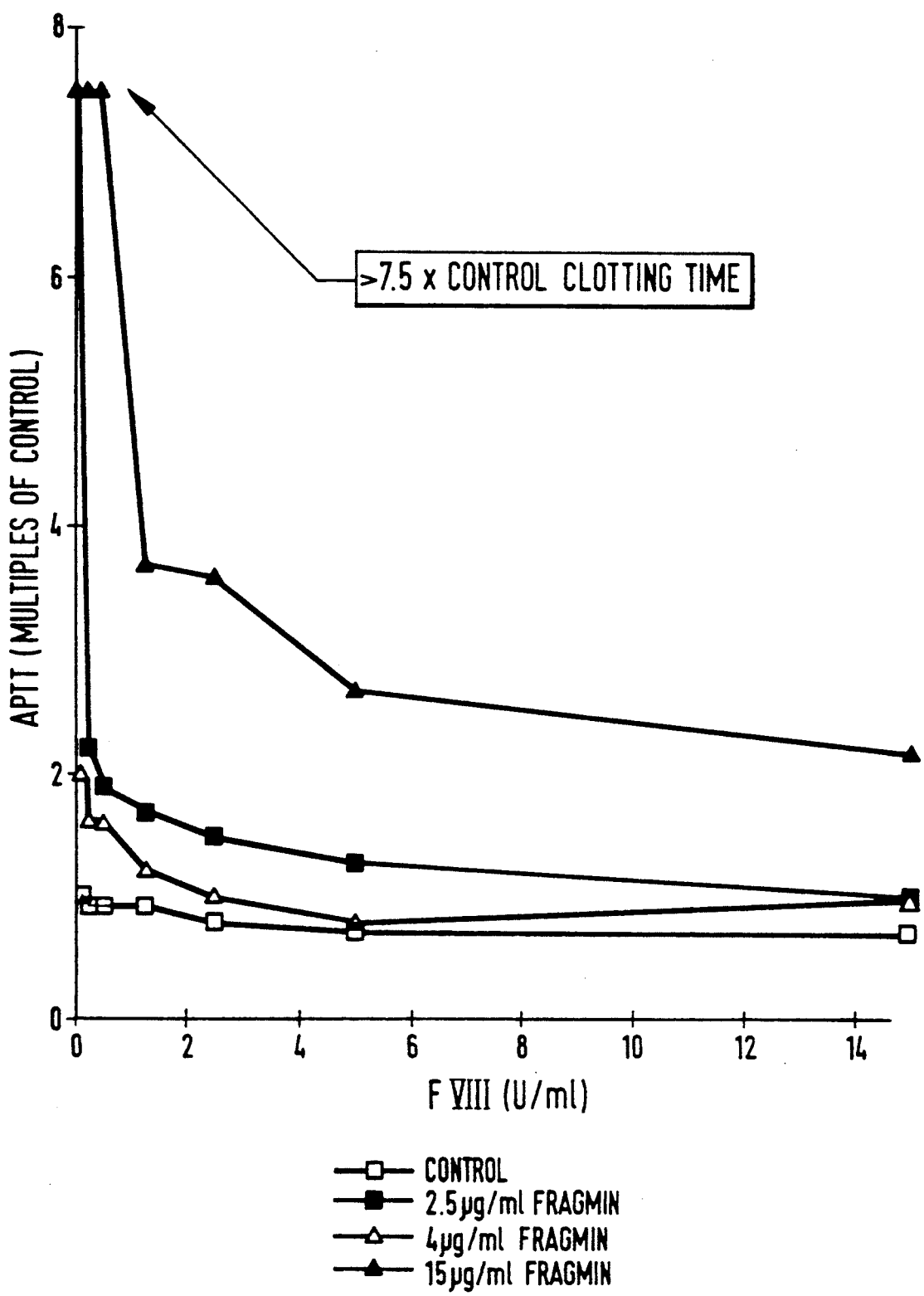

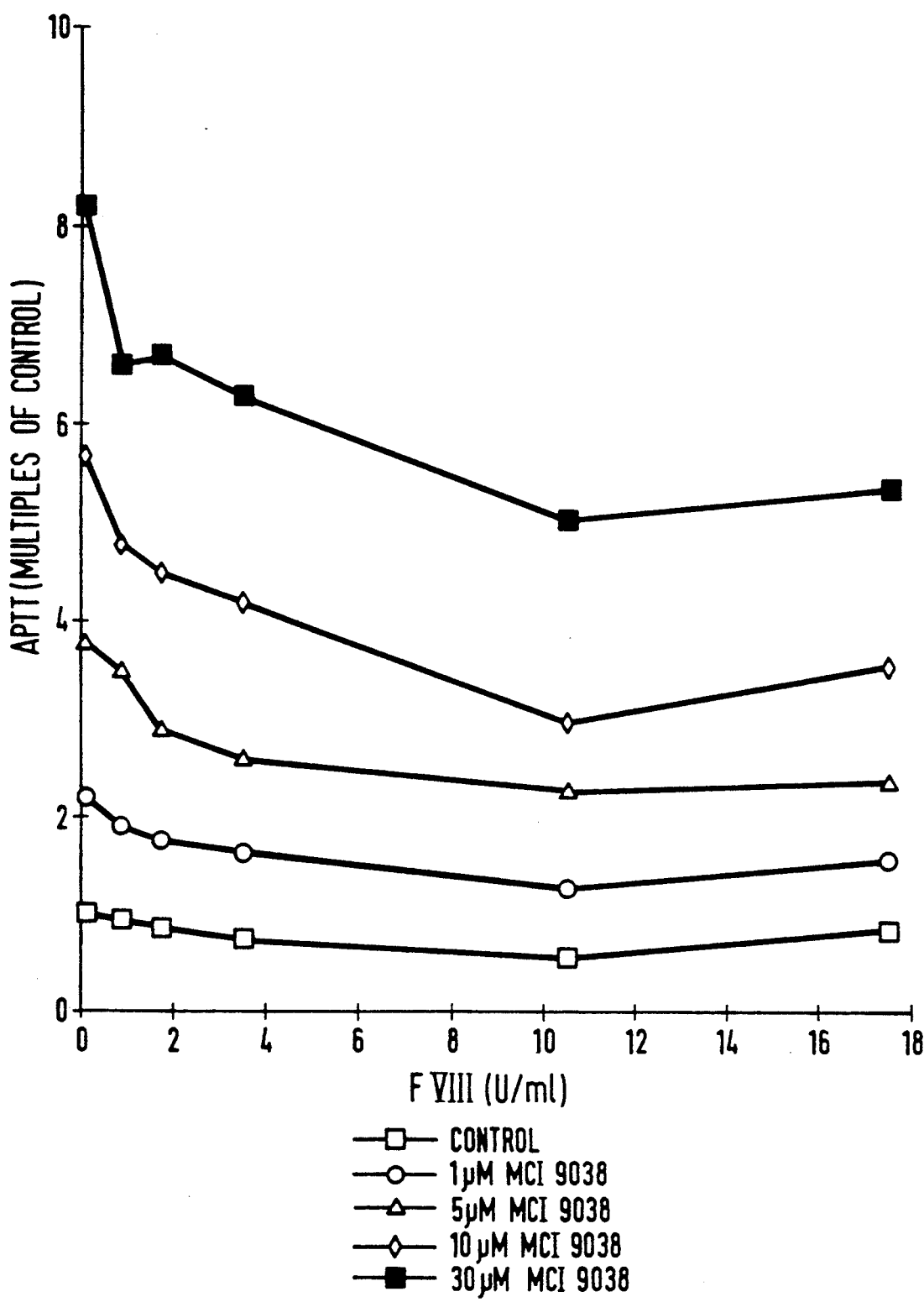

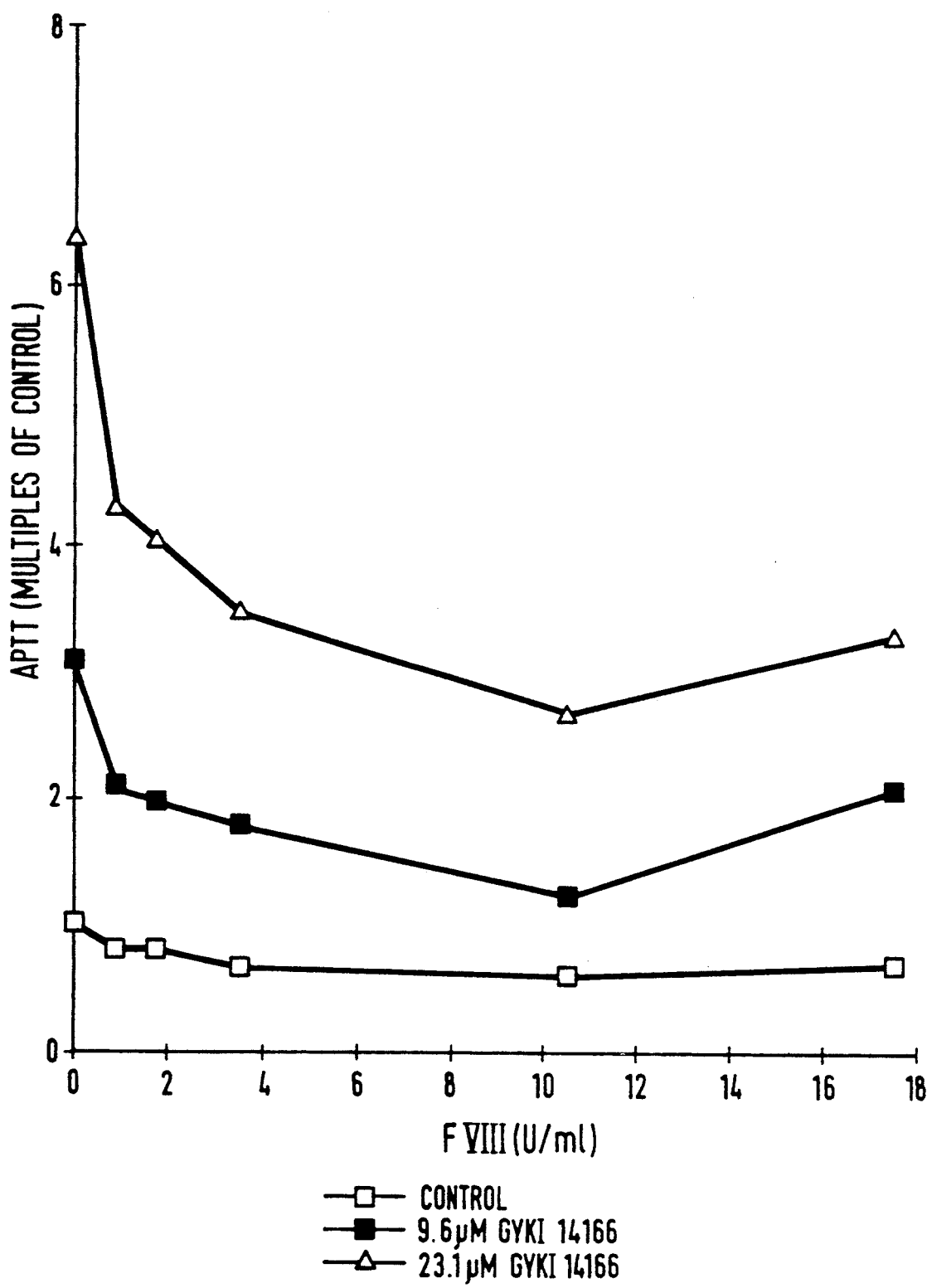

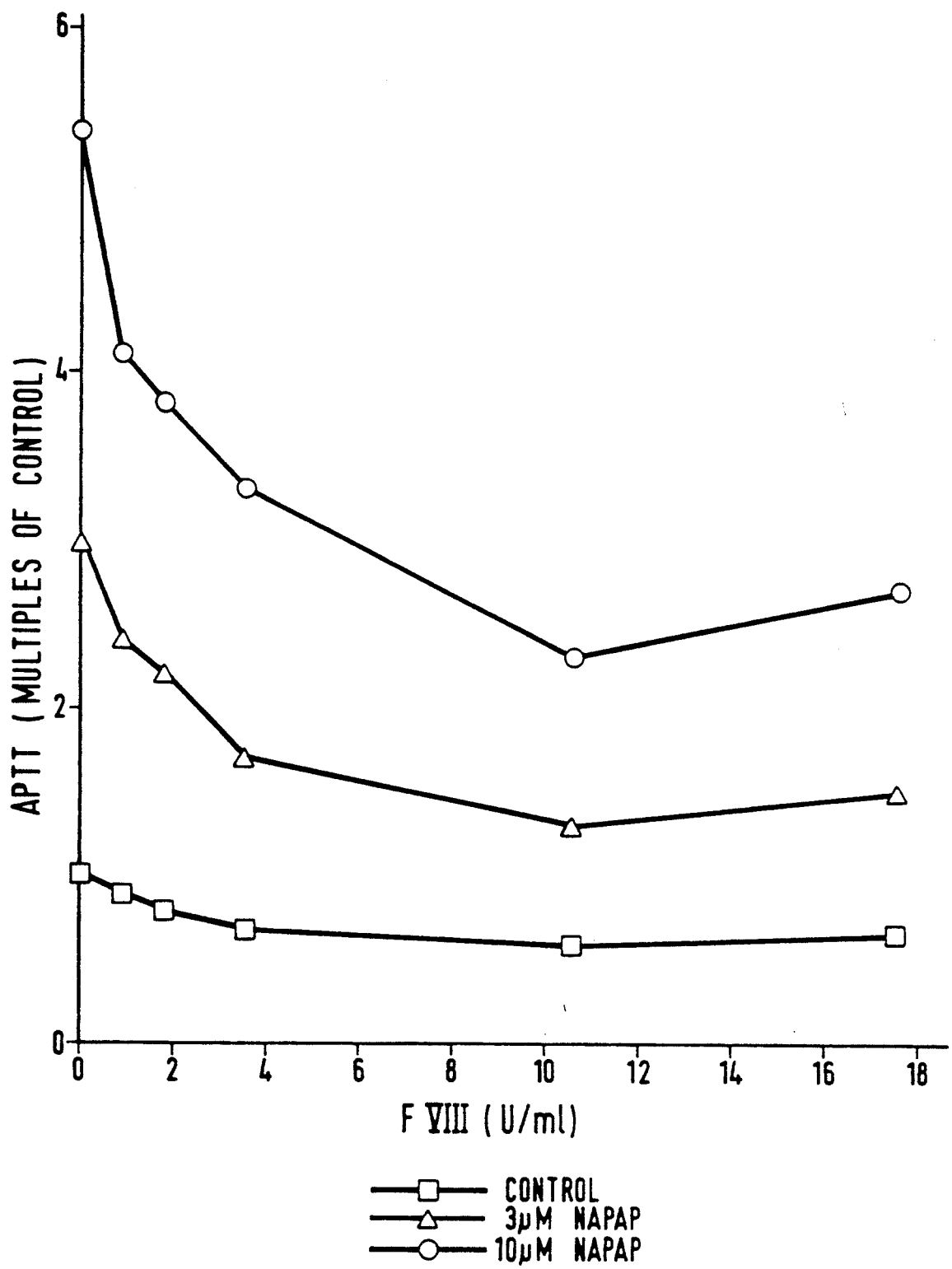

HEPARIN AND HIRUDIN ANTIDOTAL COMPOSITIONS AND METHODS

This application is a continuation of application Ser. No. 07/416,882, filed Oct. 4, 1989, now abandoned.

The present invention relates to an antidote for blood anticoagulants.

BACKGROUND OF THE INVENTION

An efficiently operating haemostatic system is of vital necessity for the mammalian organism. In the plasma of a healthy organism a dynamic equilibrium exists between the fibrinolytic system and the coagulation system, as a result of which an efficiently operating vascular network is maintained. When vascular lesions occur, the coagulation system deposits a fibrin matrix which, after achieving the haemostatic condition, is broken down again by the fibrinolytic system. In cases in which the fibrinolytic potential of the organism is not sufficient to break down intravascular thrombi that have been formed, for example in patients who suffer from thromboembolisms or post-operative complications, supporting the organism by the administration of thrombolytic agents or anticoagulants proves indispensable.

Anticoagulants like e.g. hirudin, heparin, low molecular weight heparins or low molecular weight synthetic thrombin inhibitors counteract the coagulation system by inhibiting the formation of fibrin clots. Hirudin which has been known for a long time and which occurs naturally in leeches (*Hirudo medicinalis*) (Walsman, P. and Markwardt, F. (1981) Pharmazie 36, 653) is the strongest thrombin inhibitor of all naturally occurring and synthetic anticoagulants known with a complex dissociation constant of $2 \times 10^{-14}$ M, thus preventing the formation of fibrin from its precursor fibrinogen. Other enzymes of the blood coagulation cascade are not inhibited by hirudin. In contrast to heparin which is the preferred anti-coagulant in conventional anticoagulation therapy, hirudin exerts its inhibiting action directly on thrombin and, unlike the former, does not act through antithrombin III. No effect on heart rate, respiration, blood pressure, thrombocyte count, fibrinogen and haemoglobin could be observed after intravenous administration of hirudin to dogs, even in high doses. In tests on rats, pigs and dogs, hirudin has proved effective in experimental thrombosis (induced either by stasis, vascular damage or by the injection of thrombin), in endotoxin shock, and also in DIC (disseminated intravascular coagulation).

Hirudin is not a single polypeptide species but a class of equally acting polypeptides consisting of at least four representatives designated hirudin variant 1 (HV1), hirudin variant 2 (HV2; EP Application 0 158 564), hirudin variant PA (PCT Application WO 86/03493), and "des-(Val)$_2$-hirudin" (EP Application 0 158 986). The variants differ from each other by a number of amino acids, for example at the N-terminal sequence which is Val-Val-Tyr for HV1, Ile-Thr-Tyr for HV2 and PA and Thr-Tyr for "des-(Val)$_2$-hirudin". Based on NMR studies, HV1 is composed of an N-terminal core domain with a protruding "finger" (residues 31-36), and an acidic terminal loop (Clore et al., EMBO Journal 6, 529, 1987). All abovementioned hirudin variants have an accumulation of hydrophobic amino acids at the N-terminus and an accumulation of polar amino acids at the C-terminus, a tyrosine residue (Tyr 63) present as sulphate monoester, three disulphide bridges and the anticoagulant activity in common.

Recently, cDNAs and synthetic genes coding for hirudin variants have been cloned and expressed in microbial hosts. Although the expression products lack the sulphate monoester group at Tyr63 - and were therefore designated "desulphatohirudins" - they turned out to exhibit approximately the same biological activity as the natural sulphated hirudins. De. sulphatohirudin variant HV1 has been expressed in *Escherichia coli* (European Patent Applications No. 158 564 and 168 342) and in *Saccharomyces cerevisiae* (European Patent Applications No. 168 342, 200 655, 225 633 and 252 854). Similarly, desulphatohirudin HV2 has been expressed in *Escherichia coli* (European Patent Application No. 200 655, PCT-Application No. 86/01224) and des-(Val)2-desulphatohirudin has been expressed in *Escherichia coli* (European Patent Application No. 158 986).

The main use of hirudin and other anticoagulants is for prevention or treatment of thrombi in arteries, veins or extracorporal circulation. One prerequisite for the therapeutic application of anticoagulants is the availability of an antidote highly efficient in neutralizing the anti. coagulation activity which can be used in order to survey and regulate the effect of the anticoagulant. So far, such an antidote (protamine sulphate) is available for heparin, which is therefore (despite the occurence of negative side-effects and numerous non-specific reactions) up to now the main anti. thrombotic agent used in hospitals. However, protamine sulphate is ineffective as an antidote to other anticoagulants such as hirudin, which is a much more potent antithrombotic. The reluctance to use hirudin or other anticoagulants instead of heparin in the absence of an efficient antidote could be overcome if there were an antidote available, which would rapidly reverse the anticoagulant effect and reduce the risk of haemorrhages to any patient with higher levels of anticoagulation than those desired.

OBJECT OF THE INVENTION

It is the object of the present invention to provide an antidote for blood coagulants such as hirudin. This object is achieved by the surprising finding that a plasma protein with procoagulant activity known as Factor VIII (FVIII) or a fragment thereof retaining its activity or a substance which elevates the blood concentration of FVIII acts as an antidote to anticoagulants.

DESCRIPTION OF THE INVENTION

The invention relates to the use of Factor VIII or fragments of Factor VIII which retain its activity or a substance which increases its concentration in blood for the manufacture of a medicament for use as an antidote to blood anticoagulants.

Factor VIII is a known substance originally defined as the blood clotting factor reduced or absent in a congenital bleeding disorder named haemophila A. In human plasma Factor VIII forms a non-covalently linked complex with a polymer called von Willebrand Factor (vWF). Factor VIII is a glycoprotein with a molecular weight of 260.000-280.000 d and an estimated plasma concentration of 0.05 to 0.1 ug/ml (Peake, I.R. (1984) Clinical Science 67, 561-567; Hamer, R. J. et al. (1985) Critical Rev. Oncol.-/Hematol. 6, 19-54) which is activated by thrombin and which promotes non-enzymatically the conversion of Factor X into the active enzyme Factor Xa, thus playing a key role in the series of enzymatic reactions leading to the formation of fibrin. The amino acid sequence of Factor VIII has been elucidated already several years ago (Vehar, G.A. et al. (1984) Nature 312, 337) and recombinant Factor VIII has been expressed in mammalian cell cultures (Wood, W. J. et al. (1984) Nature 312, 330). Factor VIII can be extracted fromblood or can be produced by recombinant techniques. Factor VIII as understood hereinbefore or here. inafter can be of different mammalian origin e.g. bovine or, in particular, human.

Factor VIII which is registered for administration to man as a plasma concentrate has been applied intravenously to patients with diseases caused by Factor VIII deficiencies, namely haemophila A and von Willebrands disease, in order to normalise their haemostasis and prevent bleeding associated with surgery and dental extraction (Messori, A. et al. (1987) Clinical Pharmacokinetics 13, 365–380).

Substances increasing the concentration of Factor VIII in blood are e.g. desmopressin (1-deamino-8-D-arginine vasopressin, DDAVP), adrenaline, vasopressin or insulin (review: Mannucci, P.M. (1986) in: Progress in Hemostasis and Thrombosis 8, 19–45). DDAVP is known to shorten the bleeding time and reduce blood loss in a number of haemorrhagic disease states and this is correlated with an increase in circulating Factor VIII concentrations (Kobrinsky et al. (1984) Lancet 1, 1145–1148).

DDAVP is licensed for use in man and is used clinically to treat bleeding episodes in patients with Factor VIII deficiencies and uremia. Administration can be via intravenous, subcutaneous or intranasal routes.

Prior art reports the use of DDAVP (Vigano et al. (1989) Amer. J. Hematol. 31, 32; Wijermans et al. (1989) Amer. J. Hematol. 30, 154; Kim et al. (1988) Thromb. Haem. 59, 221) and Factor VIII (Fukui et al. (1988) Blut 56, 171; Grazengel et al. (1988) Nouv. Rev. Fr. Hematol. 30, 225) in the correction of prolonged bleeding times induced by a variety of disease states. However, there are no reports of DDAVP or Factor VIII having been administered in vivo or in vitro as an antidote to overcome the effects of anticoagulants.

Both DDAVP and Factor VIII shorten the time for blood to clot in vitro by a small increment when measured by the activated partial thromboplastin time (APTT, Basu et al. (1972) N. Engl. J. Med. 287, 324). We have now found that both DDAVP and Factor VIII have a much larger effect when the clotting time is extended by addition or administration of anticoagulant drugs such as hirudin, and that this effect is large enough that they can be used as antidotes for reversal of anticoagulation by these agents.

Accordingly, the present invention provides the use of Factor VIII or fragments of Factor VIII which retain its activity or a substance which increases its concentration in blood as an antidote to blood anticoagulants.

The term fragment is intended to embrace all those peptides which share sequence homology with Factor VIII and which are either obtained by tryptic digestion of Factor VIII or by recombinant DNA technology and which retain the antihemorrhagic acitivity (e.g. EP Application No. 197 901). For example, Gervasi et al. (Arzneim. Forsch./Drug Res. 38 (II) No. 9 (1988)) state that by trypticdigestion it has been possible to obtain from bovine Factor VIII a small peptide fraction (PF) of molecular weight from 1000 to 25000 daltons devoid of procoagulant and platelet aggregating properties but endowed with a remarkable affinity for the endothelial layer of the microvessels and antihemorrhagic activity. PF showed a reduction in the bleeding time in laboratory animals including those in which the bleeding time was prolonged byheparin or acetylsalicylic acid. This occurred without interfering either with platelets or with blood coagulation. Similar fragments exhibiting corresponding properties can be obtained after tryptic digestion of human Factor VIII.

Anticoagulants for which Factor VIII or a substance which increases its concentration in blood or a fragment of Factor VIII which retains its activity act as an antidote according to the invention include hirudin, heparin, low molecular weight heparins such as fragmin, and low molecular weight synthetic thrombin inhibitors such as (2R,4R)-4-methyl-1-[$N^2$-(3-(RS)-methyl-1,2,3,4-tetrahydro-8-quinolinyl-sulphonyl)-(S)-arginyl]-2-piperidine carboxylic acid (MCI 9038; Kikumoto et al. (1984) Biochem. 33, 85), D-phenylalanyl-L-prolyl-L-arginine aldehyde sulphate (GYKI 14166; European Patent Application No. 185 390) and $N^\alpha$-(2-naphthalenesulphonyl-glycyl)-4-amidino-phenylalanine-piperidide (Kaiser et al. (1985) Biomed. Biochim. Acta 718, 1201–1210).

In the present application, the term hirudin, when not otherwise stated, is intended to embrace (1) all naturally occurring or synthetic hirudin variants and hirudin derivatives, such as hirudin fragments which retain the anticoagulant activity, and (2) all desulphatohirudin variants and desulphatohirudin derivatives, such as C-terminally shortened desulphatohirudins, which are described in the literature or are obtainable by methods of recombinant DNA technology.

Examples of such hirudins are:

(1) hirudin or a hirudin variant of type HV1 with the formula $$\begin{aligned}
&\text{H}-Z_0-Z_1-\text{Tyr}-\text{Thr}-\text{Asp}-\text{Cys}-\text{Thr}-\text{Glu}-\text{Ser}-\text{Gly}^{10}- \quad (I)\\
&-\text{Gln}-\text{Asn}-\text{Leu}-\text{Cys}-\text{Leu}-\text{Cys}-\text{Glu}-\text{Gly}-\text{Ser}-\text{Asn}^{20}-\\
&-\text{Val}-\text{Cys}-\text{Gly}-\text{Gln}-\text{Gly}-\text{Asn}-Z_2-\text{Cys}-\text{Ile}-\text{Leu}^{30}-\\
&-\text{Gly}-\text{Ser}-\text{Asp}-\text{Gly}-\text{Glu}-Z_3-\text{Asn}-\text{Gln}-\text{Cys}-\text{Val}^{40}-\\
&-\text{Thr}-\text{Gly}-\text{Glu}-\text{Gly}-\text{Thr}-\text{Pro}-Z_4-Z_5-Z_6-\text{Ser}^{50}-\\
&-Z_7-Z_8-\text{Asp}-\text{Gly}-\text{Asp}-\text{Phe}-\text{Glu}-\text{Glu}-\text{Ile}-\text{Pro}^{60}-\\
&-\text{Glu}-\text{Glu}-\text{Tyr}(R)-\text{Leu}-\text{Gln}-\text{OH},
\end{aligned}$$

wherein (R) is the phenolic hydroxygroup of Tyr (desulphatohirudin) or a —O—SO$_3$H group, and the whole molecule can be shortened by the C terminal amino acid Gln, the C—terminal dipeptide Leu—Gln, the C—terminal tripeptide Tyr—Leu—Gln or the C—terminal tetrapeptide Glu—Tyr—Leu—Gln, and wherein $Z_0$ is a direct bond or represents Val, Ile or Gly or the dipeptidyl radicals Gly-Val or Met-Val, $Z_1$ is Val, Ile or Thr, $Z_2$ is Lys, Gln, Asn, Leu, Arg or Val, $Z_3$ represents Lys, Arg, Asn, Val, Leu or Gln, $Z_4$ represents Lys, Arg, Asn, Val or Leu, $Z_5$ represents Pro or Gly, $Z_6$ and $Z_8$ independently from each other represent Gln, Asn or Met, and $Z_7$ represents His, Gln or Asn, (2) desulphatohirudin variants of type HV1 with the formula $$\text{H—Val—Val—Tyr—Thr—Asp—Cys—Thr—Glu—Ser—Gly—}^{10}$$
$$\text{—Gln—Asn—Leu—Cys—Leu—Cys—Glu—Gly—Ser—Asn—}^{20}$$
$$\text{—Val—Cys—Gly—Gln—Gly—Asn—Lys—Cys—Ile—Leu—}^{30}$$
$$\text{—Gly—Ser—Asp—Gly—Glu—Lys—Asn—Gln—Cys—Val—}^{40}$$
$$\text{—Thr—Gly—Glu—Gly—Thr—Pro—Lys—Pro—Gln—Ser—}^{50}$$
$$\text{—His—Asn—}Y_1\text{—Gly—Asp—Phe—}Y_2\text{—}Y_3\text{—Ile—Pro—}^{60}$$
$$\text{—}Y_4\text{—}Y_5\text{—}Y_6\text{—Leu—}Y_7\text{—OH,} \quad (II)$$

wherein $Y_1$ represents Asp or the radical of a neutral genetically encoded amino acid, $Y_2$ and $Y_3$ independently from each other represent Glu, Gln, Asn or the radical of a lipophilic genetically encoded amino acid, $Y_4$ and $Y_5$ independently from each other represent Glu, Gln or the radical of a neutral genetically encoded amino acid, $Y_6$ represents Tyr or the radical of an acidic genetically encoded amino acid and $Y_7$ represents Gln or the dipeptidyl radical Gln-Pro, (3) a hirudin variant of type HV2 with the formula $$\text{H—Ile—Thr—Tyr—Thr—Asp—Cys—Thr—Glu—Ser—Gly—}^{10}$$
$$\text{—Gln—Asn—Leu—Cys—Leu—Cys—Glu—Gly—Ser—Asn—}^{20}$$
$$\text{—Val—Cys—Gly—Lys—Gly—Asn—Lys—Cys—Ile—Leu—}^{30}$$
$$\text{—Gly—Ser—Asn—Gly—Lys—Gly—Asn—Gln—Cys—Val—}^{40}$$
$$\text{—Thr—Gly—Glu—Gly—Thr—Pro—Asn—Pro—Glu—Ser—}^{50}$$
$$\text{—His—Asn—Asn—Gly—Asp—Phe—Glu—Glu—Ile—Pro—}^{60}$$
$$\text{—Glu—Glu—Tyr(R)—Leu—Gln—OH,} \quad (III)$$

wherein (R) is the phenolic hydroxygroup of Tyr (desulphatohirudin) or a —O—SO$_3$H group, and Ile 1 can be replaced by Val and Thr 2 by Val (HV2 modified) or Asn 47 can be replaced by Lys or Arg or His or Tyr 63 can be replaced by Glu or Asp, (4) a hirudin variant of type PA (HV3) with the formula $$\text{H—Ile—Thr—Tyr—Thr—Asp—Cys—Thr—Glu—Ser—Gly—}^{10}$$
$$\text{—Gln—Asn—Leu—Cys—Leu—Cys—Glu—Gly—Ser—Asn—}^{20}$$
$$\text{—Val—Cys—Gly—Lys—Gly—Asn—Lys—Cys—Ile—Leu—}^{30}$$
$$\text{—Gly—Ser—Gln—Gly—Lys—Asp—Asn—Gln—Cys—Val—}^{40}$$
$$\text{—Thr—Gly—Glu—Gly—Thr—Pro—Lys—Pro—Gln—Ser—}^{50}$$
$$\text{—His—Asn—Gln—Gly—Asp—Phe—Glu—Pro—Ile—Pro—}^{60}$$
$$\text{—Glu—Asp—Ala—Tyr(R)—Asp—Glu—OH,}$$

wherein (R) is the phenolic hydroxygruop of Tyr (desulphatohirudin) or a —O—SO$_3$H group, and the polypeptide chain can be shortened at the C-terminus by 18, 10, 9, 6, 4 or 2 amino acids, or the polypeptide chain can be shortened at the N-terminus by 1 or 2 amino acids.

Examples of hirudins of the formula (I) are desulphatohirudin HV1 in which (R) is the phenolic hydroxygroup of Tyr, $Z_o$ represents Val, $Z_1$ is Val, $Z_2$, $Z_3$ and $Z_4$ are each Lys, $Z_5$ is Pro, $Z_6$ is Gln, $Z_7$ is His and $Z_8$ represents Asn, or des(Val)$_2$-desulphatohirudin, in which $Z_o$ represents a direct bond, $Z_1$ is Thr and $Z_2$-$Z_8$ and (R) are as defined for HV1. Further examples are variants of HV1 like [Asn$^{27}$]-desulphato. hirudin, [Asn$^{36}$]-desulphatohirudin, [Val$^{36}$]-desulphatohirudin, [Gly$^{48}$]-desulphatohirudin, [Met$^{49}$]-desulphatohirudin, [Met$^{52}$]-desulphatohirudin, [Asn$^{51}$]-desulphatohirudin, [Gln$^{27}$, Arg$^{47}$]-desulphatohirudin, [Gln$^{27}$, Gln$^{36}$, Arg$^{47}$]-desulphatohirudin, [Arg$^{36}$, Arg$^{47}$]-desulphatohirudin, [Arg$^{27}$, Arg$^{47}$]-desulphatohirudin, Glycyl-[Gln$^{27}$, Gln$^{36}$, Arg$^{47}$]-desulphatohirudin, Methionyl-[Gln$^{27}$, Arg$^{47}$]-desulphatohirudin, [Ile$^1$, Ile$^2$]-desulphatohirudin and [Gly$^1$]-desulphatohirudin.

Neutral genetically encoded amino acids are the following L-amino acids: Ala, Ser, Thr, Val, Leu, Ile, Asn, Gln, Met, Phe, Trp and Pro, furthermore the amino acid Gly.

Lipophilic genetically encoded amino acids are the following L-amino acids: Ala, Val, Leu, Ile, Phe and Gly.

Acidic genetically encoded amino acids are Asp and Glu.

Examples of desulphatohirudin variants of the formula (II) are [Gln$^{61,62}$]-desulphatohirudin, [Leu$^{61,62}$]-desulphatohirudin, [Asn$^{61,62}$]-desulphatohirudin, [Leu$^{57,58,61,62}$]-desulphatohirudin, [Asn$^{57,58,61,62}$]-desulphatohirudin, [Ala$^{53}$]-desulphatohirudin, [Asp$^{63}$]-desulphatohirudin, [Glu$^{63}$]-desulphatohirudin, [Pro$^{66}$]-desulphatohirudin and [Gln$^{57,58,61,62}$]-desulphatohirudin.

Examples of hirudin variants of type HV2 of the formula (III) are desulphatohirudin HV2 or desulphatohirudin HV2 (Lys47).

An example of a hirudin variant of type PA of the formula (IV) is desulphatohirudin PA.

The desulphatohirudin variants of the formulae (I), (II), (III) and (IV) can be prepared by conventional recombinant DNA technology well known in the art. Following the isolation and cloning of the hirudin gene mutation of defined codons (like e.g. base exchanges, base deletions or base extensions) within the clonedDNA is achieved in vitro bythe method ofsitedirected mutagenesis using suitable mutagenicprimers (see example 1). The resulting mutant gene is integrated in an appropriate expression vector and transformed in a microbial host like e.g. *Escherichia coli, Bacillus subtilis* or *Saccharomyces cerevisiae*. Transformants carrying the hybrid vector which preferably comprises a signal sequence linked in the proper reading frame to the DNA-sequence encoding the mutant gene are cultivated by employing conventional techniques. The desulphatohirudin variants are isolated from the culture broth and purified by means well known to anybody of ordinary skill in the art.

Factor VIII, fragments of Factor VIII, inducers of FactorVIII and blood anticoagulants are known compounds or can be prepared by conventional methods known in the art.

The invention also provides a combination preparation for separate, simultaneous or sequential use comprising (a) a composition containing a blood anticoagulant and (b) a composition containing Factor VIII or fragments of Factor VIII which retainits activity or a substance which increases its blood concentration.

The invention also provides a kit comprising a first container comprising a blood anticoagulant and a second container comprising Factor VIII or fragments of Factor VIII which retain its activity or a substance which increases its blood concentration.

The kit includes both, a composition containing a blood anticoagulant and a composition containing Factor VIII or fragments of Factor VIII which retain its activity or a substance which increases its blood concentration either as concentrates which may be further diluted prior to use or at the concentration of use, where the vials may include one or more dosages. Conveniently, single dosages may be provided in syringes, contained in sterile containers, so that the physician may employ the syringes directly, where the syringes will have the desired amount and concentration of agents. Thus, the kit may have a plurality of syringes containing a composition containing a blood anticoagulant and a plurality of syringes containing a composition containing Factor VIII or fragments of Factor VIII which retain its activity or a substance which increases its blood concentration.

The amount of F VIII or fragments of Factor VIII needed for reversing the anticoagulant effect is usually from 1oto 200 units per kg body weight, preferably from 30 to 120 units per kg body weight. One unit is that amount of F VIII found in 1 ml of normal human blood. The substance which increases the concentration of Factor VIII in blood is administered at a concentration which leads to the induction of the abovementioned amount of Factor VIII.

The therapeutically effective amount of hirudin will normally be in the dosage range from about 0.001 to 10 mg/kg of body weight, with the range from about 0.01 to 3 mg/kg of body weight being preferred.

Other anticoagulants are administered at a concentration leading to a corresponding antithrombotic activity as will be obtained with the hirudin concentrations mentioned above. Administration is made by intravenous, intramuscular or subcutaneous injection.

The above mentioned kit contains therapeutically effective amounts of Factor VIII or fragments of Factor VIII or inducer of Factor VIII and the anticoagulant.

Factor VIII or inducer of Factor VIII like DDAVP is applied according to the manufacturers specifications via a parenteral route, e.g. intravenously, subcutaneously or intranasally as and when required as an antidote to the anticoagulant. It may be administered at the same time as the anticoagulant, but will usually be administered after the anticoagulant. Administration of Factor VIII is immediately leading to the reversal of the anticoagulation, whereas DDAVP is administered 10-20 minutes prior to the desired onset of reversal of anticoagulation.

BRIEF DESCRIPTION OF THE DRAWINGS

FIG. 1 schematically illustrates the construction of plasmid pML350

FIG. 2 schematically shows the plasmid map of plasmid pJDB207/GAPFL-HIR

FIG. 3 depicts the in vitro effect of Factor VIII on APTT in human plasma containing hirudin FIG. 4 depicts the in vivo effect of increasing concentrations of Factor VIII on hirudin induced elevation of APTT in the rat FIG. 5 depicts the in vivo effect of Factor VIII on the duration of action of hirudin in the rat FIG. 6 depicts the effect of Factor VIII on elevated rat plasma APTT induced by hirudin infusion FIG. 7 depicts the in vitro effect of DDAVP infusion on Factor VIII levels in human plasma and the corresponding effect on hirudin induced elevation of APTT in vitro FIGS. 8 to 12 depict the in vitro effect of Factor VIII on APTT in human plasma containing different anticoagulants (FIG. 8: heparin; FIG. 9: fragmin; FIG. 10: (2R,4R)-4-methyl-1-[$N^2$-(3-(RS)-methyl-1,2,3,4-tetrahydro-8-quinolinyl-sulphonyl)-(S)-arginyl]-2-piperidine carboxylic acid; FIG. 11: D-phenylalanyl-L-prolyl-L-arginine aldehyde sulphate; FIG. 12:$N^\alpha$-(2-naphthalenesulphonyl-glycyl)-4-amidino-(RS)-phenylalaninepiperidide)

The following examples illustrate the invention without implying any limitations. In Examples 2 to 6 the hirudin used is desulphatohirudin HV1, and the Factor VIII used is that sold under the Trade Mark KRYOBULIN TIM 3.

EXAMPLE 1

Production of Desulphatohirudin HV1 variants

A. Construction of the Plasmid pML350 (see FIG. 1)

a) Digestion of the DNA of plasmid pIN-III-ompA-2

10 μg of plasmid pIN-III-ompA-2 [J. Ghrayeb et al., EMBO-J. 3, 2437 (1984)] are dissolved in 25 μl of 100 mM Tris-HCl pH 7.5, 50 mM NaCl and 100 μg/ml gelatine and are digested with the restriction endonucleases EcoRI and BamHI. The solution is adjusted to TNE and extracted with phenol/chloroform. The DNA is precipitated with ethanol. The vector DNA pIN-III-ompA-2/EcoRI/BamHI is isolated after electrophoresis in agarose by gel elution.

b) Digestion of the DNA of plasmid pML310

20 μg of the plasmid pML310 (see European Patent Application No. 168 342) are digested in 50 μl of 100 mM Tris-HCl pH 7.5, 50 mM NaCl and 100 μg/ml gelatine with the restriction endonucleases EcoRI and BamHI. The solution is adjusted to TNE and extracted with phenol/chloroform. The DNA is precipitated with ethanol. The $F_1 1 \propto F_2$–DNA (hirudin gene) is isolated after gel electrophoresis in agarose by gel elution.

c) Ligation of the $F_1$-$F_2$-DNA (hirudin gene) from pML310 with the vector DNA pIN-III-ompA-2/EcoRI/BamHI ug of $F_1$-$F_2$-DNA (hirudin gene)/EcoRI/BamHI and 30 µg of the vector DNA pIN-III-ompA-2/EcoRI/BamHI are dissolved in 50 µl of 100 mM Tris-HCl pH 7.5, 50 mM NaCl and 100 µg/ml gelatine, adjusted to TNE. The solution is extracted with phenol/chloroform and the DNA is precipitated with ethanol. The DNA precipitate is dissolved in 20 µl of a solution of 50 mM Tris-HCl (pH 7.8), 10 mM $MgCl_2$, 10 mM DTT, 0.5 mM ATP, and 100 µg/l gelatine and treated with 25 units/µl $T_4$ DNA ligase (Biolabs) at 15° C. for 3 h. By this way the recombinant plasmid pML350 is created, which contains the $F_1$-$F_2$-DNA (hirudin gene) inserted. d) Transformation of E. coli HB101 with plasmid pML350 The E. coli HB101 cells pretreated with calcium that are prepared as described by Mandel et al. [J. Mol. Biol. 53, 159 (1970)].

The solution obtained in c), which contains the recombinant plasmid pML350, is heated at 65° C. for 10 min in order to inactivate the $T_4$ DNA ligase and is then cooled to 37° C. 10 µl of the resulting reaction mixture are added to 150 µl of calcium-treated E. coli HB101 cells in 10 mM $MgCl_2$ and 10 mM Tris.HCl (pH 7.5) in a total volume of 200 µl.

Subsequently, this mixture is cooled in ice for 30 min, heated for 2 min at 42° C. and then left to stand for 50 min in 1 ml of L-medium (Bacto tryptone 10 g/l; Bacto yeast extract 5 g/l; NaCl 5 g/l; glucose 5 gl; ampicillin 0.1 g/l) at 37° C. The mixture is then spread out in aliquots of 0.2 ml on 5 agar plates (McConkey Agar, Difco), which contain 60 µg/ml of ampicillin (Serva). The agar plates are then maintained at 37° C. for 16–18 hours. 185 ampicillin resistant colonies of transformed E. coli HB101 cells are obtained.

e) Screening the colonies that contain $F_1$-$F_2$-DNA 6 transformed colonies are pressed off onto nitrocellulose filter B85 (Schleicher and Schull). In accordance with Grunstein and Hogness [Proc. Natl. Acad. Sci. USA 72, 3961 (1979)] the colonies are lysed and their denatured DNA is fixed on the filter. Subsequently prehybridization of the filters is carried out in 20 ml (per filter) of $4 \times SET$ [=solution of 30 mM Tris.HCl (pH 8), 150mM NaCl, 1 mMEDTA], 0.1% (w/v) Ficoll 400 (Pharmacia), 0.5% SDS, 50µg/ml denatured calf thymus DNA for 4 h at 64° C. Subsequently the nitrocellulose filters are treated in 20 ml (per filter) of $5 \times SET$ (w/v), 0.1% (w/v) Ficoll 400, 0.2% SDS and 50 µl/ml denatured calf thymus DNA for 16 h at 64° C. with the $^{32}P$ radioactively labelled probe (approximately $10^3$–$10^4$ Cerencov cpm per filter). A mixture consisting of oligonucleotides 46/64 complementary, 1/58, 96/67 and 154/64 complementary (see European Patent Application No. 168 342) is used as probe.

Subsequently, the filters are washed twice in $2 \times SET$, 0.2% SDS at room temperature, then twice in $2 \times SET$, 0.5% SDS at 60° C. (first for 30 min, then for 60 min). The filters are then dried between 3 MM paper (Whatman) and placed at −80° C. on an X-ray film (Fuji) with an intensifying screen (Ilford) for 1–2 days.

The resulting autoradiogram shows 5 positive colonies (clones) which can be used for further processing, one of which received the designation pML350.

B. Construction of Plasmid pBH109

As plasmid pML350 originates from plasmid pIN-III-ompA-2 including a multi-cloning linker (EcoRI, HindIII, BamHI sites) it contains 12 additional base pairs in front of the mature hirudin gene coding for Ala, Gln, Phe, Met. To get mature desulphatohirudin expressed these 12 base pairs are looped out by in vitro mutagenesis making use of a 27meroligonucleotide.

a) Preparation of pML350/XbaI/BamHI (SI)

5 µg of plasmid pML350 are digested with the endonucleases XbaI and BamHI. The larger of the two XbaI-BamHI fragments (SI) is isolated by gel elution after electrophoresis on agarose and dissolved in 1 mM Tris-HCl pH 7.5, 0.1 mM EDTA.

b) Preparation of pML350/PvuI (SII)

5 ug of plasmid pML350 are digested with the endonuclease PvuI. The linearized DNA pML350/PvuI is subsequently digested with 3 units of intestinal alcaline phosphatase (Boehringer) for 30 min at 37° C. The enzyme is inactivated by heating the solution for 60 min at 65° C. The linear pML350/PvuI (SII) DNA is isolated by gel elution after electrophoresis on agarose and dissolved in 1 mM Tris-HCl pH 7.5, 0.1 mM EDTA.

c) Preparation of the oligonucleotide (27 mer) I27

In analogy to the procedure described in European Patent Application No. 168 342 the following DNA fragment (designated I27) has been synthesized:

5'-GTA GCG CAG GCC GTT GTT TAC ACC GAC-3'
I27

The phosphorylation at the 5' ends was done with $[\gamma\text{-}^{32}P]$-ATP and $T_4$ polynucleotide kinase (Boehringer) as described [Molecular Cloning, A Laboratory Manual (ed. T. Maniatis et al.), Cold Spring Harbor Lab. (1982), p. 125].

d) Construction of plasmid pBH109

0.3 ug each of SI DNA and of SII DNA are mixed with 40 pmol of the phosphorylated DNA fragment I27 in 27 µl of 1 mM Tris-HCl pH 7.5, 0.1 mM EDTA. To the mixture 3 µl of $10 \times$ polymeraseligase buffer (1M NaCl, 65 mM Tris-HCl pH 7.5, 80 mM $MgCl_2$ and 10 mM β-mercaptoethanol) are added. This mixture is heated for 3 min in a boiling water bath to denature the DNA fragments. Subsequently, the mixture is gradually cooled (about 1° C./min) to 30° C. and incubated at this temperature for 30 min. Further the mixture is incubated at 4.C for 30 min and afterwards for 10 min in ice.

12 µl of the four deoxyribonucleotide phosphates (7.5 mM each), 6 µl of 10 mM ATP, 6 µl of $T_4$ DNA ligase (2.5 U/µl) and 1.2 µl of Klenow DNA polymerase (Boehringer, 5 U/µl) are added and the DNA mixture (total volume 55 µl) is incubated for 16 h at 12.5° C.

The DNA mixture is digested with 2 units of endonuclease EcoRI for 1 h at 37° C. in order to destroy unchanged starting plasmid pML350. With this procedure, plasmid pBH109 is formed. Plasmid pBH109 contains the lpp promoter and the lac promoter/operator operably linked to the ompA-2 signal sequence linked in frame to the gene coding for mature desulphatohirudin.

e) Transformation of E. coli HB101 with plasmid pBH109

The transformation with calcium treated E. coli HB101 cells is done as described above. The total reaction mixture used is 55 µl.

f) Screening of the colonies which contain plasmid pBH109

100 transformed colonies are cultivated, from each colony plasmid DNA is prepared and digested with EcoRI. All plasmid DNAs, which are not digestable with EcoRI are potent plasmids pBH109 which is lacking the EcoRI site.

Two positive identical colonies have been identified. One of them is selected and designated pBH109.

The correct sequence of the $F_1$-$F_2$-DNA following the ompA-2 leader sequence is confirmed by sequence analysis.

C. Mutation of the Residue Lys27 of Hirudin to Asn27 Using Single Stranded M13mc19/Hirudin.

```
                    24    26    28    30
coding strand      Gln  Gly  Asn  Lys  Cys  Ile  Leu
of hirudin      5' CAG  GGT  AAC  AAA  TGC  ATC  CTG 3' mutagenic
primer 1        3' GTC  CCA  TTG  TTA  ACG  TAG  GAC 5' mutated         5' CAG  GGT  AAC  AAT  TGC  ATC  CTG 3'
coding strand      Gln  Gly  Asn  Asn  Cys  Ile  Leu
```

Mutagenic primers are synthesised using the phosphoramidite method [M.H. Caruthers, in Chemical and Enzymatic Synthesis of Gene Fragments (H.G. Gassen and A. Lang, Eds.) Verlag Chemie, Weinheim, Federal Republic of Germany] on an Applied Biosystems (Model 380B) synthesiser.

I. Preparation of M13mp19/Hirudin

XbaI-BamHI cut M13mp19DNA

To 5 μl M13mp19 double stranded DNA (ds-DNA; 0.1 μg/ml; BRL) are added 2 μl React 2 (500 mM Tris-HCl, pH 8.0; 100 mM MgCl₂, 500 mM NaCl) (BRL), 1 μl XbaI (10 U/μl), 0.5 μlBamHI (10 U/μl) and 12 μl H₂O. After incubation at 37° C. for 1.5 h, 0.5 μl BamHI, 2.5 μl React 3 (500 mM Tris-HCl, pH 8.0; 100 mM MgCl₂; 1000 mM NaCl) (BRL), and 2 μl H₂O are added and incubation is continued at 37° C. for 1 h. The volume is made up to 100 μl with H₂O. The ds-DNA is isolated by phenol extraction and ethanol precipitation, and dissolved in 30 μl of TE buffer (Tris-HCl 10 mM, EDTA 1 mM, pH 8.0).

Insert DNA

Five μg of the plasmid pBH109 are cut with XbaI and BamHI as described above and the digest is electrophoresed for 3 h at 150 volt using a 3.5% polyacrylamide gel with 1×TBE buffer (10×TBE buffer: 108 g Tris, 55 g boric acid, 9.3 g EDTA.2H₂O/l). The XbaI-BamHI fragment containing thehirudin gene (250 bp) isvisualised under UV light afterimmersing the gel in 400 ml 1×TBE buffer containing 10 μl ofethidium bromide solution (10 μg/ml in water). The part of the gel containing the restriction fragment is cut from the gel and placed in a dialysis bag with 500 μl of 0.5×TBE, and the DNA is electroeluted in a BIO-RAD minigel electrophoresis apparatus using 0.5×TBE as the running buffer at 170 volt for 30 min. The DNA is loaded onto an Elutip-d column (Schleicher & Schull) equilibrated with 0.5×TBE. The column is washed with 2 ml of 0.5×TBE and the DNA is eluted with 1 M NaCl in 0.5×TBE (1 ml). The DNA is precipitated with ethanol and redissolved in 10 μl of TE buffer.

Ligation of XbaI-BamHI hirudin insert into M13mp19 and preparation of single stranded DNA Five μl XbaI-BamHI hirudin insert, 2 μl XbaI-BamHI cut M13mp19, 1 μl 10×ligase buffer (50 mM Tris-HCl, pH 7.5, 10 mM MgCl₂, 10 mM dithiothreitol), 1 μl ATP, 1.5 μl T4 DNA ligase (BRL; 1 U/μl) are mixed and incubated overnight at 14° C. Five μl ofligation mixture are used to transform E. coli JM101 competent cells according to the method of J. Messing [Methods in Enzymology 101, 21–78 (1983)]. Twelve clear plaques are picked and single stranded DNA (ss-DNA) is prepared from each plaque as described by J. Messing (supra). The DNA designated M13mp19/hirudin is redissolved in 50 μl of TE buffer (0.1-0.5 μg/l).

II Site-Directed Mutacenesis

Phosphorylation of mutagenic primer 200 pmol (23 μl) of mutagenic primer 1 (see above) is phosphorylated by adding 3 μl 10×kinasebuffer (lM Tris-HCl, 0.1 M MgCl₂, 0.1 M dithiothreitol, pH 8.3) 3 μl 10 mM ATP and1 1 μl T4 polynucleotide kinase (BRL, 10 U/μl). After incubation at 37° C. for 1 h, the reaction is stopped by heating at 65° C. for 10 min.

Annealing of the mutagenic primer 1 to the single-stranded M13mp19/hirudin template Six μl (0.5 μg) of single-stranded M13mp19/hirudin is incubated with 3 μl (20pmol) of the phosphorylated mutagenic oligodeoxyribonucleotide (6.6 pmol/ul) and 1 μl buffer A (0.2M Tris-HCl, pH 7.5, 0.lM MgCl₂, 0.5M NaCl, 0.01M DTT) at 70° C. for 5 min, and cooled slowly to room temperature over 30 min.

Extension-ligation reaction

To the above annealed mix is added 1 μl buffer B (0.2 M Tris-HCl, pH 7.5, 0.1 M MgCl₂, 0.01 M DTT), 1 μl 10mM ATP, 4 μl 2mM dNTP mixture, 5 μl T4 DNA polymerase (Boehringer, 1 U/μl), 5 μl T4 DNA ligase (BRL, 1 U/μl). This mixture is incubated at 16° C. for 3 h. The reaction is stopped by incubating at 65° C. for 10 min.

Transformation and preparation of single-stranded mutant DNA

The ligation mixture is diluted 1:20 with sterile H₂O, and 1 μl, 5 μl, as well as 1 μl undiluted ligation mixture is used to transform competent E. coli BMH 71-81 mut S cells [B. Kramer, W. Kramer and H.-J. Fritz, Cell 38, 879–887 (1984)]. The cells are plated out as described in the "M13 cloning and sequencing Handbook" (published by Amersham). Twelve colourless plaques are picked and ss-DNA is prepared as described above.

Screening of single-stranded DNA for mutant

To screen for mutated single-stranded DNA, each of the 2 ss-DNAsamples is sequenced by the dideoxynucleotide chain termination method [F. Sanger, S. Nickler and A. R. Coulson, Proc. Natl. Acad. Sci. USA 74. 5463–5467 (1977)]. Initially, only the dideoxynucleotide complementary to the expected mutated base is used in the reaction. Subsequently, the ss-DNA from several positive mutants are sequenced to establish the full DNA sequence of the mutant using T7 DNApolymerase (Sequenase, USB) following the method of Tabor and Richardson Proc. Natl. Acad. Sci. USA 84, 4767–4771 (1987)]. The expected base change encoding Lys → Asn mutation at position 27 of the recombinant hirudin are observed in theDNA sequence. The phage DNA having the expected sequence is designated M13mp19/hirudin K27N.

Preparation of replicative form (RF) DNA from single-stranded M13mp19/hirudin K27N phage DNA Competent E. coli JM101 cells are transformed with 10-20 ng of single-stranded hirudin K27N mutant DNA and ds-DNA is prepared as described in the "M13 cloning and sequencing Handbook" (published by Amersham). A yield of 40-50 μg of ds-DNA is obtained from 100 ml of culture.

Isolation of Mutant Hirudin XbaI-BamHI insert

The mutated hirudin XbaI-BamHI insert is cut out of 25 μg of the ds-DNA and purified as described in section IB. The DNA is dissolved in 20 μl of sterile water.

Preparation of XbaI-BamHI cut pIN-III-ompA-2 vector DNA

A digest of approximately 1.5 μg pIN-III-ompA-2 plasmid is made by adding 6 μl React 2 buffer (BRL), 2 μl (20 Units) XbaI, 1 μl BamHI (10 Units), 1 μl EcoRI (10 Units) and 37 μl H₂O (total volume 50 μl), and incubation for 3 h at 37° C. 1μl (10 Units) BamHI, 1 μl (10 Units) EcoRI, 5 μlReact 3 (BRL) and 12 μl H₂O are added and incubation continued for 1 h at 37° C.

Ligation of mutant hirudin K27N XbaI-BamHI insert DNA into XbaI-BamHI cut pIN-III-ompA-2 plasmid Nine ul hirudin K27N XbaI-BamHI insert DNA, 2 μl XbaI-BamHI cut pIN-III-ompA-2 vector DNA, 3 μl 10×ligation buffer (BRL) and 1 μl (1 U/μl) T4 DNA ligase (BRL) are mixed and incubated at 14° C. for 16-20 h.

III. Expression of variant [Asn²⁷]-desulphatohirudin in *E. coli* JM101. Transfection into *E. coli* strain JM101

Five μl of ligation mixture is used to transform 0.3 ml of *E. coli* JM101 competent cells according to the method of J. Messing (supra). Three ml of 2×YT/Ampicillin (50 μg ampicillin/ml 2×YT) is added to the sample and the cells allowed to grow at room temperature for 1 h. A 1 ml sample of the culture is then taken and poured onto an LB/Ampicillin (50 μg ampicillin/ml LB-agar) plate and grown overnight at 37° C. The transforming plasmid DNA is referred to as pIN-III-ompA-2/HIR-K27N.

Selection of [Asn²⁷]-desulphatohirudin expressing colonies

Ten bacterial colonies from the LB/Ampicillin plates are picked and grown separately for 5 h at 37° C. in 5 ml LB/Ampicillin (50 μg Ampicillin/ml LB). 1 ml samples are taken from each culture tube and the cells recovered by centrifugation (3000×g for 5 min). Each sample of cells is osmotically shocked by treatment with 100 μl of 10 mM Tris-HCl, pH 8.1 for 30 min at 0° C. to release the material in the periplasmic space of the bacteria. The cells are removed by centrifugation as before, and the supernatant is tested for hirudin activity. The sample which gives the highest inhibitory activity is selected for batch culture.

Batch culture and isolation of [Asn²⁷]-desulphatohirudin

The remaining quantity (4 ml) of cells from the most active sample is used to inoculate 1 l of LB/Ampicillin (50 μg Ampicillin/ml LB). The culture is grown overnight at 37° C., and the cells are recovered by centrifugation (3000×g for 15 min.). The cell pellet is osmotically shocked by resus. pension in 50 ml of 10 mM Tris-HCl, pH 8.1 at 0° C. for 1 h. The cells are removed from the periplasmic fraction bycentrifugation at 6000×g for 10 min.

Purification of [Asn²⁷]-desulphatohirudin

The pH of the periplasmic fraction is adjusted to 6.5 with 0.1 M HCl and filtered through a 0.45 μm filter (Nalgene). The protein is loaded onto a Mono-Q column FPLC system (Fast Protein Liquid Chromatography, Pharmacia-LKB) equilibrated with 50mMbis-Tris-HCl buffer pH 6.5. The desulphatohirudin mutant is eluted from the column using a linear salt gradient of 0-300 mM NaCl in bis-Tris-HCl pH 6.5 over 45 min. 0.8 ml fractions of the column eluate are collected and tested for hirudin activity as described above. The desulphatohirudin mutant-containing fractions are pooled, filtered as above and chromatographed on a Millipore-Waters HPLC system using a Brownlee Labs C8 reversed-phase HPLC column equilibrated with 0.09% (v/v) trifluoroacetic acid in H₂O. The hirudin mutant is eluted from the column with a linear gradient of 7 to 28% (v/v) acetonitrile in 0.09% (v/v) trifluoroacetic acid in H₂O. [Asn²⁷]-desulphatohirudin having a purity of about or more than 98% elutes as a single peak at 28 min.

D. Mutation of the Residue Lys 27 of Hirudin to Gln 27, and of the Residue Lys 47 to Arg 47

A: Mutation of Lys 27 to Gln 27

```
                                    27
coding strand       Gln Gly Asn Lys Cys Ile Leu
of hirudin      5' CAG GGT AAC AAA TGC ATC CTG 3' mutagenic       3' GTC CCA TTG GTT ACG TAG GAC 5'
primer 2A mutated         5' CAG GGT AAC CAA TGC ATC CTG 3'
coding strand      Gln Gly Asn Gln Cys Ile Leu
```

B: Mutation of Lys 47 to Arg 47

```
                                    47
coding strand       Gly Thr Pro Lys Pro Gln Ser
of hirudin      5' GGT ACC CCG AAA CCG CAG TCT 3' mutagenic       3' CCA TGG GGC TCT GGC GTC AGA 5'
primer 2B mutated         5' GGT ACC CCG AGA CCG CAG TCT 3'
coding strand      Gly Thr Pro Arg Pro ln  Ser
```

The procedures given above are repeated using mutagenic primers 2A and B to obtain and characterize the desired variant protein in which Lys 27 is replaced by Gln 27 and Lys 47 by Arg 47. The transforming plasmid DNA is referred to as pIN-III-ompA-2/HIR-K27Q,K47R. The variant is designated [Gln²⁷, Arg⁴⁷]-desulphatohirudin.

E. Mutation of the Residue Lys 27 of Hirudin to Gln 27, the Residue Lys 36 to Gln 36, and of the Residue Lys 47 to Arg 47 a: Mutation of Lys 36 to Gln 36

```
                    34      36      38
coding strand       Asp Gly Glu Lys Asn Gln Cys
of hirudin      5' GAC GGT GAA AAA AAC CAG TGC 3' mutagenic       3' CTG CCA CTT GTT TTG GTC ACG 5'
primer 3 mutated         5' GAC GGT GAA CAA AAC CAG TGC 3'
coding strand      Asp Gly Glu Gln Asn Gln Cys
``` b: Mutation of Lys 27 to Gln 27

The mutation of Lys 27 to Gln 27 is performed according to D (above).

c: Mutation of Lys 47 to Arg 47

The mutation of Lys 47 to Arg 47 is performed according to D (above).

The procedures given above are repeated using mutagenic primers 2A, 3 and 2B to obtain and characterize the desired variant protein in which Lys 27 is replaced by Gln 27, Lys 36 is replaced by Gln 36 and Lys 47 is replaced by Arg 47. The transforming plasmid DNA is referred to as pIN-III-ompA-2/HIR-K27Q,K36Q,K47R. The variant is designated [Gln$^{27}$, Gln$^{36}$, Arg$^{47}$]-desulphatohirudin.

F. Extension of the N-Terminus of [Gln$^{27}$, Arg$^{47}$]-desulphatohirudin with a Methionine Residue

```
                           1         3         5
coding strand    signal seq.    Val Val Tyr Thr Asp Cys
of hirudin    5' GCG CAG GCC ... GTT GTT TAC ACC GAC TGC 3' mutagenic
primer 4      3' CGC GTC CGG TAC CAA CAA ATG TGG CTG ACG 5' mutated       5' GCG CAG GCC ATG GTT GTT TAC ACC GAC TGC 3'
coding strand    signal seq.   Met  Val Val Tyr Thr Asp Cys
```

The procedures given above are repeated using mutagenic primers 2A, 2B and 4 to obtain and characterize the desired variant protein in which the N-terminus of [Gln$^{27}$, Arg$^{47}$]-desulphatohirudin is extended by Met. The protein is designated methionyl-[Gln$^{27}$, Arg$^{47}$]-desulphatohirudin.

G. Mutation of the Residues Glu 57,58,61,62 of Hirudin to Gln 57,58,61,62

```
                   56            58          60          62         64
coding strand    Gly Asp Phe Glu Glu Ile Pro Glu Glu Tyr Leu Gln
of hirudin    5' GTT GAC TTC GAA GAA ATC CCG GAA GAA TAC CTG CAG 3' mutagenic
primer 5      3' CCA CTG AAG GTT GTT TAG GGC GTT GTT ATG GAC GTC 5' mutated       5' GGT GAC TTC CAA CAA ATC CCG CAA CAA TAC CTG CAG 3'
coding strand    Gly Gly Phe Gln Gln Ile Pro Gln Gln Tyr Leu Gln
```

The procedures given above are repeated using mutagenic primer 5 to obtain and characterize the desired variant protein in which Glu 57,58,61,62 are replaced by Gln 57,58,61,62. The variant is designated [Gln$^{57,58,61,62}$]desulphatohirudin.

H. Construction of a Yeast Expression Plasmid Coding for [Pro$^{66}$]-Desulphatohirudin The DNA sequence coding for desulphatohirudin is extended by the oligonucleotide CCA, which codes for proline. The result. ing new desulphatohirudin is expressed in yeast. It contains 66 aminoacids with a proline at its C-terminal end. This poly. peptide is referredto as [Pro$^{66}$]-desulphatohirudin.

Yeast expression plasmid pJDB207/GAPFL-HIR (see FIG. 2; European patent application No. 225 633) is digested with restriction endonucleases SalI and EcoRI. The 478 bp SalI-EcoRI fragment is separated on a 0.8% preparative agarose gel in TBE buffer (90 mM Tris-base, 90 mM boric acid, 2.5 mM EDTA pH 8.3). The ethidiumbromide-stained fragment is isolated from the gel. The DNA is electroeluted in 0.2×TBE buffer for 45 min at 100 mA and purified by DE52 (Whatman) ion exchange chromatography. The DNA is eluted from the DE52 column with a high salt buffer (1.5 M NaCl, 10 mM Tris-HCl pH 8.0, 1 mM EDTA), precipitated with ethanol and redissolved in H$_2$O at a concentration of 0.1 pmoles/ul. The 478 bp SalI-EcoRI fragment contains the SalI-BamHI sequence of pBR322 fused to the BglII-EcoRI GAPFL promoter fragment.

Plasmid pJDB207/GAPFL-HIR is digested with BamHI and SalI. The large, 6.7 kb vector fragment is isolated as described above. The small, 740 bp SalI-BamHI fragment is also isolated. It contains the sequence of the 478 bp SalI-EcoRI fragment (see above) in addition to the PH05 signal sequence fused in frame to the coding sequence of desulphatohirudin. The 740 bp fragment is digested with AsuII. The DNA is extracted with phenol/chloroform, precipitated with ethanol and redissolved in H$_2$O.

A synthetic oligodeoxynucleotide of the formula

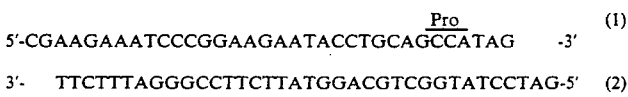

5'-CGAAGAAATCCCGGAAGAATACCTGCAGCCATAG   -3'   (1)

3'-   TTCTTTAGGGCCTTCTTATGGACGTCGGTATCCTAG-5'   (2)

is kinased in 40 μl of 60 mM Tris-HCl pH 7.5, 10 mMMgCl$_2$, 5 mM DTT, 0.5 mM ATP and 27 U of T4 polynucleotide kinase (Boehringer) for 45 min at 37° C. The reaction mixtures for oligonucleotides (1) and (2) are combined. The mixture is heated for 10 min at 75° C. and allowed to cool to room temperature. The annealed oligonucleotide linker (1+2) is stored at −20° C.

0.85 μg (3.8 pmoles) of the AsuII digested DNA are incubated for 16 h at 15° C. with a 100 fold excess of the kinased and annealed oligonucleotide linker over DNA ends in 150 μl of 60 mM Tris-HCl pH 7.5, 10 mM MgCl$_2$, 5 mM DTT, 3.5 mM ATP and 1200 U of T4 DNA ligase (Biolabs). After inactivation of the T4 DNA ligase for 10 min at 85.C the excess linkers are removed by precipitation of the DNA in the presence of 10 mM EDTA, 300 mM sodium acetate pH 6.0 and 0.54 volumes of iso. propanol. The DNA is digested with EcoRI and BamHI. The resulting fragments are separated on a 2% preparative agarose gel in TBE buffer. The 262 bp fragment is recovered from the gel by electroelution and ethanol precipitation. The DNA is resuspended at a concentration of 0.1 pmoles/μl. The EcoRI-BamHI fragment contains the coding sequence ofde. sulphatohirudin with the additional CCA triplet coding for Pro 66.

Three DNA fragments, isolated as described above, are ligated in the following reaction: 0.2 pmoles of the 478 bp SalI-EcoRI fragment, 0.2 pmoles of the 262 bp EcoRI-BamHI fragment and 0.1 pmoles of the 6.7 kb vector fragment are ligated in 10 μl of 60 mM Tris-HCl pH 7.5, 10 mM $MgCl_2$, 5 mM DTT, 1 mM ATP and 200 U of T4 DNA ligase for 6 h at 15° C. A one μl aliquot of the ligation mixture is added to 100 μl of calcium-treated, transformation competent *E. coli* HB101 cells.

12 transformed, ampicillin-resistant colonies are grown in LB medium containing 100 mg/l of ampicillin. Plasmid DNA is prepared [Holmes et al., Anal. Biochem. 114 (1981), 193] and analysed by BamHI, EcoRI double digests. The presence of the mutation in the DNA is confirmed by DNA sequencing [Sanger et al., Proc. Natl. Acad. Sci. USA74 (1977) 5463]. One clone with the CCA codon in the hirudin structural gene is referred to as pJDB207/GAPFL-HIR (Pro 66).

I. Mutation of the residues Val 1,2 of hirudin to Ile 1,2

```
                                     1         3         5
coding strand        signal seq.    Val  Val  Tyr  Thr  Asp  Cys
of hirudin      5' GCG  CAG  GCC  GTT  GTT  TAC  ACC  GAC  TGC 3' mutagenic
primer 6        3' CGC  GTC  CGG  TAA  TAA  ATG  TGG  CTG  ACG 5' mutated         5' GCG  CAG  GCC  ATT  ATT  TAC  ACC  GAC  TGC 3'
coding strand        signal seq.    Ile  Ile  Tyr  Thr  Asp  Cys
```

The procedures given above are repeated using mutagenic primer 6 to obtain and characterize the desired variant protein in which the N-terminal amino acids Val 1,2 are replaced by Ile 1,2. The variant is designated [$Ile^{1,2}$]desulphatohirudin.

J. Mutation of the Residues Val 1 of hirudin to GlV 1

```
                                     1         3         5
coding strand        signal seq.    Val  Val  Tyr  Thr  Asp  Cys
of hirudin      5' GCG  CAG  GCC  GTT  GTT  TAC  ACC  GAC  TGC 3' mutagenic
primer 7        3' CGC  GTC  CGG  CCA  CCA  ATG  TGG  CTG  ACG 5' mutated         5' GCG  CAG  GCC  GTT  GTT  TAC  ACC  GAC  TGC 3'
coding strand        signal seq.    Gly  Val  Tyr  Thr  Asp  Cys
```

The procedures given above are repeated using mutagenic primer 7 to obtain and characterize the desired variant protein in which the N-terminal amino acid Val 1 is replaced by Gly 1. The variant is designated [$Gly^1$]-desulphatohirudin.

In an analogous manner applying the procedures detailed in Example 1 any other desired variant of HV1 , HV2 and PA can be produced.

EXAMPLE 2

In Vitro Effect of Factor VIII on APTT in Human Plasma Containing Hirudin

The anticoagulant effects of hirudin are measured in vitro on human plasma to which various concentrations of hirudin (in saline) have been added, one minute prior to APTT determination (Activated partial thromboplastin time; means for measuring blood clotting according to Basu et al. (1972) N. Engl. J. Med. 287, 324). Different concentrations of FVIII (reconstituted in water in accordance with the manufacturers specification) are added and the results are shown in FIG. 3 of the accompanying drawings. The anticoagulant effects of hirudin are measured by APTT. The results show the reduction in the anticoagulant effect of hirudin irrespective of the degree of anticoagulation as compared to a volume matched saline control using untreated human plasma with no hirudin added.

EXAMPLE 3

In Vivo Effect of Increasing Concentrations of Factor VIII on Hirudin Induced Elevation of APTT in the Rat Rats are dosed intravenously (1 ml/kg) via the tail vein with different bolus doses of hirudin using saline as a vehicle to give different levels of anticoagulation. Where applicable the rats are given different doses of FVIII (reconstituted in water in accordance with the manufacturers specifications) by simultaneous application. The results are shown in FIG. 4 which illustrates the reduction in anticoagulation. Results are compared to a volume matched saline control.

EXAMPLE 4

In Vivo Effect of Factor VIII on the Duration of Action of Hirudin in the Rat Rats are dosed intravenously (1 ml/kg) via the tail vein with a bolus dose of hirudin (3 mg/kg) resulting in high levels of anticoagulation at early time points. At times of 2 minutes and 10 minutes after the hirudin treatment, the rats are given 120 U/kg of FVIII intravenously (2–4 ml/kg). The FVIII is reconstituted in water according to the manufacturers specifications. The results are shown in FIG. 5 and clearly demonstrate that FVIII reduces the duration of action of the hirudin as compared to the effects of a volume matched saline control.

EXAMPLE 5

Effect of Factor VIII on Elevated Rat Plasma APTT Induced by Hirudin Infusion Hirudin (in saline) is infused via the jugular vein into rats at a rate of 0.0125 mg/kg/min giving an anticoagulation level of about 2.5 times control APTT. 20 Minutes into the infusion VIII (reconstituted in water in accordance with the manufacturers specification) was dosed at 30, 60 and 120 U/kg intravenously as a bolus via the tail vein. The results are shown in FIG. 6 and clearly demonstrate a significant reduction in APTT within 5 minutes of the injection. Results are compared to a volume matched saline control.

EXAMPLE 6

In Vitro Effect of DDAVP Infusion on Factor VIII Levels in Human Plasma and the Corresponding Effect on Hirudin Induced Elevation of APTT in Vitro 1-Deamino-8-D-arginine vasopressin (DDAVP) (0.3 mg/kg in sterile saline) is infused into human volunteers over a 15 minute period between times 0–15 minutes. Subsequently blood samples are taken and FVIII levels measured (Langdell et al. (1953) J. Lab. Chim. Med. 41, 637) and the correspond. ing effect on hirudin induced elevation of APTT in vitro asessed. The results are shown in FIG. 7 which represent a typical example of ten volunteer studies. The results show that DDAVP raised FVIII levels and hence reduces the degree of anticoagulation induced by hirudin. Results are compared to volume matched saline controls.

EXAMPLES 7-11

In Vitro Effect of Factor VIII on APTT in Human Plasma Containing Different Anticoagulants Example 2 was repeated except that the following anticoagulants were used instead of hirudin.

| Example | Anticoagulant |
|---------|---------------|
| 7 | Heparin |
| 8 | Fragmin |
| 9 | (2R,4R)-4-methyl-1-(N$^2$-3-(RS)-methyl-1,2,3,4-tetrahydro-8-quinolinyl-sulphonyl)-(S)-arginyl)-2-piperidine carboxylic acid (MCI 9038; Kikumoto et al. Biochem. 33, 85 (1984) |
| 10 | D-Phenylalanyl-L-prolyl-L-arginine aldehyde sulphate (GYKI 14166; European Patent Application No. 185 390) |
| 11 | N$^\alpha$-(2-naphthalenesulphonyl-glycyl)-4-amidino-(RS)-phenylalaninepiperidide (NPAP; Kaiser et al. (1985) Biochem. Biophys. Acta 44, 1201) |

The results are shown in FIGS. 8–12 which clearly demonstrate the reduction in the anticoagulant effect of different anti. coagulants tested by the addition of Factor VIII.

EXAMPLE 12

Pharmaceutical Preparations

Desulphatohirudin HV1 is dissolved in 0.9% NaCl solution to a final concentration of 0.2 mg/ml or 2 mg/ml. The solution is passed through a bacteriological filter (0.22 μm pore size), and the filtrate is portioned out and introduced under aseptic conditions into sterile 2 ml ampoules.

50.000 Units of Factor VIII are dissolved in 20 ml physiological saline solution, the solution is sterilized by ultrafiltration and portioned out into sterile 2 ml ampoules.

The sterilized solutions can be used directly, for example for intravenous administration.

We claim:

1. A method of at least partially reversing the anticoagulation activity of a blood anticoagulant in a mammal comprising administering to said mammal a therapeutically effective amount of Factor VIII or fragments of Factor VIII which retain its activity or a substance which increases its concentration in blood, wherein the blood anticoagulant is selected from the group consisting of heparin, anticoagulantly active heparin fragments, low molecular weight heparins, fragmin, thrombin inhibitors, hirudin, synthetic hirudin variants, hirudin derivatives, hirudin fragments, desulphatohirudin variants, (2R, 4R)-4-methyl-1-[N$^2$-(3-(RS)-methyl-1,2,3,4-tetrahydro-8-quinolinyl-sulphonyl)-(S)-arginyl]-2-piperidine carboxylic acid, D-phenyl-alanyl-L-prolyl-L-arginine aldehyde sulphate, and N$\alpha$-(2-naphthalene-sulphonyl-glycyl)-4-amido-phenylalaninepiperidine.

2. The method of claim 1, wherein the anticoagulant is hirudin.

3. The method of claim 1, wherein the anticoagulant is selected from the group consisting of heparin, anticoagulantly active heparin fragments, low molecular weight heparins, fragmin, and thrombin inhibitors.

4. The method of claim 1, wherein the anticoagulant is selected from the group consisting of low molecular weight heparins, and low molecular weight thrombin inhibitors.

5. The method of claim 1, wherein the anticoagulant is selected from the group consisting of hirudin, synthetic hirudin, variants, derivatives and fragments thereof and desulphatohirudin variants and derivatives.

6. The method of claim 1, wherein the anticoagulant is desulphatohirudin HV1.

7. The method of claim 1, wherein the anticoagulant is heparin.

8. The method of claim 1, wherein the anticoagulant is fragmin.

9. The method of claim 1, wherein the anticoagulant is a low molecular weight thrombin inhibitor selected from the group consisting of (2R,4R)-4-methyl-1-[N$^2$-(3-(RS)-methyl-1,2,3,4-tetrahydro-8-quinolinyl-sulphonyl)-(S)-arginyl]-2-piperidine carboxylic acid, D-phenyl-alanyl-L-prolyl-L-arginine aldehyde sulphate, and N$\alpha$-(2-naphthalenesulphonyl-glycyl)-4-amido-phenylalanine-piperidine.

10. The method of claim 1, wherein, the substance which increases Factor VIII is 1-deamino-8-D-arginine vasopressin.

* * * * *

REEXAMINATION CERTIFICATE (2632nd)

United States Patent [19]

Findlay et al.

[11] B1 5,204,323

[45] Certificate Issued    Jul. 18, 1995

[54] HIRUDIN ANTIDOTAL COMPOSITIONS AND METHODS

[75] Inventors: Valerie S. Findlay; Roger Kerry, both of Horsham; Graham F. Pay, Patcham; Robert B. Wallis, Leechponds Hills; Keith D. Butler, Soreham-by-Sea, all of England

[73] Assignee: Ciba-Geigy Corporation, Ardsley, N.Y.

Reexamination Request:
No. 90/003,585, Sep. 30, 1994

Reexamination Certificate for:
Patent No.: 5,204,323
Issued: Apr. 20, 1993
Appl. No.: 763,477
Filed: Sep. 20, 1991

Related U.S. Application Data

[63] Continuation of Ser. No. 416,882, Oct. 4, 1989, abandoned.

[30]    Foreign Application Priority Data

Oct. 6, 1988 [GB] United Kingdom ........... 8823480

[51] Int. Cl.⁶ ............... A61K 38/02; A61K 31/725
[52] U.S. Cl. ........................... 514/2; 514/12; 514/54; 514/56; 514/834; 530/383
[58] Field of Search ............ 514/2, 12, 54, 56, 834; 530/383

[56]    References Cited

U.S. PATENT DOCUMENTS 4,789,733  12/1988  Winkelman ............... 514/8
4,929,602  5/1990   Harker et al. ............ 514/18

FOREIGN PATENT DOCUMENTS 0229234  7/1987  European Pat. Off. .

OTHER PUBLICATIONS

Thrombosis and Hemostasis 59, 221–224.
Glynn, *Amer. J. Clin. Path.*, vol. 71:397–400, (1979).
Tornebohm et al., *Thrombosis Research*, vol. 45:635–643, (1987).
Agnelli et al. *Chem. Abstracts* 111(15):1273825 (1989).
Palmer et al. *Chem. Abstracts* 109(25):222834h (1988).
Koehler et al. *Chem. Abstracts* 109(7):512220 (1988).
Rock et al. *Chem. Abstracts* 95(19):162771r (1981).
Rock et al. *Vox Sang.* 41:56–60 (1981).
Palmer et al. *Transfusion* 28(4):311–315 (1988).
Agnelli et al. *Thrombosis and Haemostasis* 61(3):507–510 (1989).
*Thrombos. Diather. Haemorrh.* vol. 14, No. 32, p. 32 (1965).
Textbook of Medical Physiology, Arthur C. Guytan, MD pp. 140–141.
Peake *Clinical Science* 67, pp. 561–567, (1984).
Vehar et al. *Nature* 312, pp. 337–342, (1984).
Hamer et al. *Critical Reviews Ancol./Hermatol.* 6, pp. 19–54, (1985).
Messori et al. *Clinical Pharmacokinetics*, 13, pp. 365–380, (1987).
Fukui et al. *Blut* 56, pp. 171–178, (1988).
Mannucci *Hemeostasis and Thrombosis*, 8, pp. 19–45, (1986).
Wigermans et al. *Amer. J. Hematol.* 30, pp. 154–157, (1989).
Vigano et al. *Amer. J. Hemat.* 31, pp. 32–35, (1989).
Schröder et al. *Pharmazeutische Chemie* pp. 650–659, (1982).
Kobrinsky et al. *The Lancet* pp. 1145–1148, (1984).
*Die Pharmayie*, 36, pp. 653–660, (1981).

*Primary Examiner*—Douglas W. Robinson

[57]    ABSTRACT

The invention provides an antidote to blood anticoagulants comprising Factor VIII or fragments of Factor VIII which retain its activity or a substance which increases its concentration in blood.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 7 and 8 are cancelled.

Claims 1, 3 and 4 are determined to be patentable as amended.

Claims 2, 5, 6, 9 and 10, dependent on an amended claim, are determined to be patentable.

1. A method of at least partially reversing the anticoagulation activity of a blood anticoagulant in a mammal comprising administering to said mammal a therapeutically effective amount of Factor VIII or fragments of Factor VIII which retain its activity or a substance which increases its concentration in blood, wherein the blood anticoagulant is selected from the group consisting of [heparin, anticoagulantly active heparin fragments, low molecular weight heparins, fragmin,] thrombin inhibitors, hirudin, synthetic hirudin variants, hirudin derivatives, hirudin fragments, desulphatohirudin variants, (2R,4R)-4-methyl-1-[$N^2$-(3-(RS)-methyl-1,2,3,4-tetrahydro-8-quinolinyl-sulphonyl)-(S)-arginyl]-2-piperidine carboxylic acid, D-phenyl-alanyl-L-prolyl-L-arginine aldehyde sulphate, and $N\alpha$-(2-naphthalene-sulphonyl-glycyl)-4-amido-phenylalaninepiperidine.

3. The method of claim 1, wherein the anticoagulant is selected from the group consisting of [heparin, anticoagulantly active heparin fragments, low molecular weight heparins, fragmin, and] thrombin inhibitors.

4. The method of claim 1, wherein the anticoagulant is [selected from the group consisting of low molecular weight heparins, and] *a* low molecular weight thrombin [inhibitors] *inhibitor*.

* * * * *